(12) United States Patent
French et al.

(10) Patent No.: US 6,900,022 B1
(45) Date of Patent: May 31, 2005

(54) PROSTATE CANCER-SPECIFIC MARKER

(75) Inventors: Cynthia K. French, Irvine, CA (US); Karen K. Yamamoto, San Clemente, CA (US); A. Said El Shami, Camarillo, CA (US)

(73) Assignee: Diagnostic Products Corporation, Los Angeles, CA (US)

( * ) Notice: Subject to any disclaimer, the term of this patent is extended or adjusted under 35 U.S.C. 154(b) by 0 days.

(21) Appl. No.: 09/680,121

(22) Filed: Oct. 4, 2000

Related U.S. Application Data

(63) Continuation of application No. 09/036,315, filed on Mar. 6, 1998, and a division of application No. 09/535,597, filed on Mar. 27, 2000.
(60) Provisional application No. 60/041,246, filed on Mar. 7, 1997, and provisional application No. 60/047,811, filed on May 15, 1997.

(51) Int. Cl.$^7$ ............... G01N 33/574; G01N 33/53; G01N 33/48
(52) U.S. Cl. ............... 435/7.23; 435/7.1; 436/64
(58) Field of Search ............... 435/7.1, 7.23, 435/69.1, 325, 320.1; 436/64; 536/23.1, 23.5

(56) References Cited

U.S. PATENT DOCUMENTS 6,218,523 B1 * 4/2001 French et al.

FOREIGN PATENT DOCUMENTS

EP 725139 A2 7/1996

OTHER PUBLICATIONS

Branch, Andrea D., "A good antisense molecule is hard to find," TIBS 23, pp. 45–50 Feb. 1998.
Eerola, Ritta et al., "Expression of Prostate Specific Antigen on the Surface of a Filamentous Phage," Biochem. And Biophys. Res. Comm. vol. 200, No. 3, May 16, 1994 pp. 1346–1352.
Flanagan, W. Michael et al., "Cellular penetration and antisense activity by a phenoxazine–substituted heptanucleotide," Nature Biotech 17:48–52 Jan. 1999.
Hilbush, Brian S. et al., "A third synaptotagmin gene, Syt3, in the mouse," PNAS, vol. 91, pp. 8195–8199 Aug. 1994.
Sharief,Farida S. et al., "Human Prostatic Acid Phosphatase: cDNA Cloning Gene Mapping and Protein Sequence Homology with Lysosomal Acid Phospbatase," Biochem. And Biophys. Res. Comm. vol. 160, No. 1, Apr. 14, 1989, pp. 79–86.
Ullrich, Beate et al., "Functioanl Properties of Multiple Synaptotagmins in Brain," Neuron, vol. 13, pp. 1281–1291, Dec. 1994.
Vician, Linda et al., "Synaptotagmin IV is an immediate early gene induced by depolarization in PC12 cells and in brian," PNAS, vol. 92, pp. 2164–2168, Mar. 1995.
Walent, Jane H. et al., "A Novel 145 kd Brain Cystosolic Protein Reconstitutes Ca2+ –Regulated Secretion in Permeable Neuroendocrine Cells," Cell, vol. 70, pp. 765–775, Sep. 4, 1992.

* cited by examiner

*Primary Examiner*—Gary B. Nickol
(74) *Attorney, Agent, or Firm*—Joseph E. Mueth

(57) ABSTRACT

This invention provides cDNA encoding a prostate-cancer specific marker, Repro-PC-1.0, Repro-PC-1.0 polypeptides and methods for use in diagnosis and therapy.

3 Claims, 6 Drawing Sheets

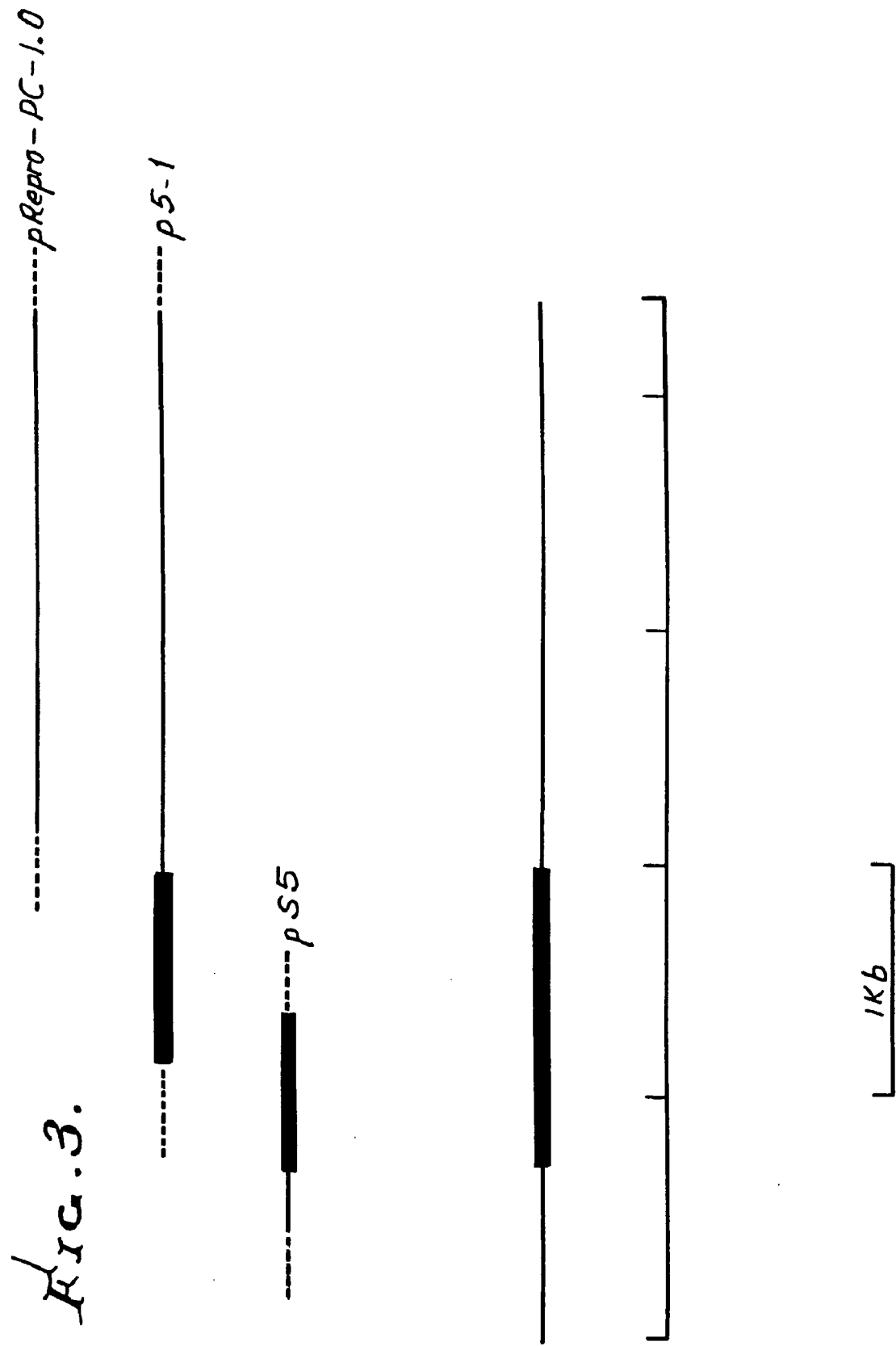

FIG. 5.

```
PC1  :   1 MAPITTSREEFDEIPTVVGIFSAFGLVFTVSLFAWICCQRKSSKSNKTPPYKFVHVLKGV  60
             |||||||| ||||||||||||||||||||||||||||||| |||||||||||||||||
SYT4 :   1 MAPITTSRVEFDEIPTVVGIFSAFGLVFTVSLFAWICCQRRSAKSNKTPPYKFVHVLKGV  60

PC1  :  61 DIYPENLNSKKKKFGADDKNEVQNKPAVPKNSLHLDLEKRDLNGNFPKINLKPGSPSDLEN 120
             |||||| |||||||| ||  |  :|  : | ||||||||||||||||| ||| ||||||
SYT4 :  61 DIYPENLSSKKKKFGDDDKSEAKRKAALPNLSLHLDLEKRDLNGNFPKINPKAGSSSDLEN 120

PC1  : 121 ATPKLFLEGEKESVSPESLKSSTSLTSEEKQEKLGTLFFSLEYNFERKAFVVNIKEARGL 180
             ||||| || ||| ||||||||||||||||||||||||||||||||| |||||||| ||
SYT4 : 121 VTPKLFPETEKEAVSPESLKSSTSLTSEEKQEKLGTLFLSLEYNFEKKAFVVNIKEAQGL 180

PC1  : 181 PAMDEQSMTSDPYIKMTILPEKKHKVKTRVLRKTLDPAFDETFTFYGIPYTQIQELALHF 240
           |||||||||||||||||||||||||||||||||||| |||||||||| |||:|||:||
SYT4 : 181 PAMDEQSMTSDPYIKMTILPEKKHKVKTRVLRKTLDPVFDETFTFYGVPYPHIQELSLHF 240

PC1  : 241 TILSFDRFSRDDIIGEVLIPLSGIELSEGKMLMNREIIKRNVRKSSGRGELLISLCYQST 300
             | ||||||||| ||| |||||||||| ||||| ||||||| ||||||||| |||||||
SYT4 : 241 TVLSFDRFSRDDVIGEVLVPLSGIELSDGKMLMTREIIKRNAKKSSGRGELLVSLCYQST 300

PC1  : 301 TNTLTVVLKARHLPKSDVSGLSDPYVKVNLYHAKKRISKKKTHVKKCTPNAVFNELFVF 360
           ||||||||||||||||||||||||||||||||||||||||||||||||||||||||||
SYT4 : 301 TNTLTVVLKARHLPKSDVSGLSDPYVKVNLYHAKKRISKKKTHVKKCTPNAVFNELFVF 360

PC1  : 361 DIPCEGLEDISVEFLVLDSERGSRNEVIGQLVLGAAAEGTGGEHWKEICDYPRRQIAKWH 420
           ||||| |||:||||||||||||||||||||| ||||  :||:|| |||| ||||||||| ||
SYT4 : 361 DIPCESLEEISVEFLVLDSERGSRNEVIGRLVLGATAEGSGGGHWKEICDFPRRQIAKWH 420

PC1  : 421 VLCDG 425
           :||||
SYT4 : 421 MLCDG 425
```

```
PKC-C2            154 ENVPSLCGCDHTERRGRIYLEINVKENLLTVQIKEGRNL-IPMDPNGLSDPYVKVKLIPDD
Repro-PC-1.0 "B"  276 BIIKRNVRKSSGRGELLISLCYQSTINTLTVVLKARHL-PKSDVSGLSDPYVKVNLYHAK
SYNAPTOTAGMIN "B" 268 ---QEKLGDICFSLRYVPTAGKLTVVILEARNL-KKMDVGGLSDPYVKIHLMQNG
SYNAPTOTAGMIN "A" 134 ----KEEPKEEEKLGKLQYSLDYDFQNNQLLVGIIQAAELPA-LDMGGTSDPYVK-----VFL
Repro-PC-1.0 "A"  150 ----------KQEKLGTLFFSLEYNFERKAFVVNIKEARGLPAMDEQSMTSDPYIK-----MTI PKC-C2            214 KDQSKKK--TRTTKACLNPVWNE--TLTYDLKPEDKDRRILIEVWDWDRTSRNDFMGALSF
Repro-PC-1.0 "B"  336 KRISKKK--THVKKCTPNAVFNELFVF-DIPCEGLEDISVBEflVLDSERGSRNEVIG--QL
SYNAPTOTAGMIN "B" 322 KRLKKKK--TTIKKNTLNPYYNESFSF-EVPFEQIQKVQVVVTVLDYDKIGKNDAIG--KV
SYNAPTOTAGMIN "A" 187 LPDKKKKFEBTKVHREKTLNPVFNENEQFTE-KVPYSELGGKTLVMAVYDFDRFSKhDIIGEFKV
Repro-PC-1.0 "A"  199 LPEKKHKVKTRVLRKTLDPAFDETFTFYGIPYTQIQELALHFTILSFDRFSRDDIIGEVLI PKC-C2            271
Repro-PC-1.0 "B"  392 VLGAA
SYNAPTOTAGMIN "B" 378 FVGYN
SYNAPTOTAGMIN "A" 247 PMNTVDF
Repro-PC-1.0 "A"  260 PLS
```

FIG. 6.

SEQUENCE LISTING

```
<160> NUMBER OF SEQ ID NOS: 27

<210> SEQ ID NO 1
<211> LENGTH: 3891
<212> TYPE: DNA
<213> ORGANISM: Homo sapiens
<220> FEATURE:
<221> NAME/KEY: CDS
<222> LOCATION: (151)..(1425)
<220> FEATURE:
<223> OTHER INFORMATION: product = Repro-PC-1.0

<400> SEQUENCE: 1
ctctttgcct cctccctgtt ccaggagctg gtgccctggg ctctgcgctg ttgttttcag        60
cgttccgaaa gccggcgctt gagatccagg caagtgaatc cagccaggca gttttccctt       120
cagcacctcg dacagaacac gcagtaaaaa atg gct ccg atc acc acc agc cgg       174
                                  Met Ala Pro Ile Thr Thr Ser Arg
                                    1               5 gaa gaa ttt gat gaa atc ccc aca gtg gtg ggg atc ttc agt gca ttt       222
Glu Glu Phe Asp Glu Ile Pro Thr Val Val Gly Ile Phe Ser Ala Phe
        10                  15                  20 ggc ctg gtc ttc aca gtc tct ctc ttt gca tgg atc tgc tgt cag aga       270
Gly Leu Val Phe Thr Val Ser Leu Phe Ala Trp Ile Cys Cys Gln Arg
    25                  30                  35                  40 aaa tca tcc aag tct aac aag act cct cca tac aag ttt gtg cat gtg       318
Lys Ser Ser Lys Ser Asn Lys Thr Pro Pro Tyr Lys Phe Val His Val
                45                  50                  55 ctt aag gga gtt gat att tac cct gaa aac cta aat agc aaa aag aag       366
```

-continued

| | | |
|---|---|---|
| Leu Lys Gly Val Asp Ile Tyr Pro Glu Asn Leu Asn Ser Lys Lys Lys<br>              60                    65                      70 | | |
| ttt gga gca gat gat aaa aat gaa gta aag aat aag cca gct gtg cca<br>Phe Gly Ala Asp Asp Lys Asn Glu Val Lys Asn Lys Pro Ala Val Pro<br>           75                    80                    85 | 414 |
| aag aat tca ttg cat ctg gat ctt gaa aag aga gat ctc aat ggc aat<br>Lys Asn Ser Leu His Leu Asp Leu Glu Lys Arg Asp Leu Asn Gly Asn<br>           90                    95                 100 | 462 |
| ttt ccc aaa acc aac ctc aaa cct ggc agt cct tct gat ctg gag aat<br>Phe Pro Lys Thr Asn Leu Lys Pro Gly Ser Pro Ser Asp Leu Glu Asn<br>105                    110                    115                 120 | 510 |
| gca acc ccg aag ctc ttt tta gaa ggg gaa aaa gag tca gtt tcc cct<br>Ala Thr Pro Lys Leu Phe Leu Glu Gly Glu Lys Glu Ser Val Ser Pro<br>          125                    130                 135 | 558 |
| gag agt tta aag tcc agc act tcc ctt act tca gaa gag aaa caa gag<br>Glu Ser Leu Lys Ser Ser Thr Ser Leu Thr Ser Glu Glu Lys Gln Glu<br>              140                    145                 150 | 606 |
| aag ctg gga act ctc ttc ttc tcc tta gaa tac aac ttc gag aga aaa<br>Lys Leu Gly Thr Leu Phe Phe Ser Leu Glu Tyr Asn Phe Glu Arg Lys<br>          155                    160                 165 | 654 |
| gca ttt gtg gtc aat atc aag gaa gcc cgt ggc ttg cca gcc atg gat<br>Ala Phe Val Val Asn Ile Lys Glu Ala Arg Gly Leu Pro Ala Met Asp<br>          170                    175                 180 | 702 |
| gag cag tcg atg acc tct gac cca tat atc aaa atg acg atc ctc cca<br>Glu Gln Ser Met Thr Ser Asp Pro Tyr Ile Lys Met Thr Ile Leu Pro<br>185                    190                    195                 200 | 750 |
| gag aag aag cat aaa gtg aaa act aga gtg ctg aga aaa acc ttg gat<br>Glu Lys Lys His Lys Val Lys Thr Arg Val Leu Arg Lys Thr Leu Asp<br>                  205                    210                 215 | 798 |
| cca gct ttt gat gag acc ttt aca ttc tat ggg ata ccc tac acc caa<br>Pro Ala Phe Asp Glu Thr Phe Thr Phe Tyr Gly Ile Pro Tyr Thr Gln<br>          220                    225                 230 | 846 |
| atc caa gaa ttg gcc ttg cac ttc aca att ttg agt ttt gac agg ttt<br>Ile Gln Glu Leu Ala Leu His Phe Thr Ile Leu Ser Phe Asp Arg Phe<br>              235                    240                 245 | 894 |
| tca aga gat gat atc att ggg gaa gtt cta att cct ctc tcg gga att<br>Ser Arg Asp Asp Ile Ile Gly Glu Val Leu Ile Pro Leu Ser Gly Ile<br>250                    255                    260 | 942 |
| gaa tta tct gaa gga aaa atg tta atg aat aga gag atc atc aag aga<br>Glu Leu Ser Glu Gly Lys Met Leu Met Asn Arg Glu Ile Ile Lys Arg<br>265                    270                    275                 280 | 990 |
| aat gtt agg aag tct tca gga cgg ggt gag tta ctg atc tct ctc tgc<br>Asn Val Arg Lys Ser Ser Gly Arg Gly Glu Leu Leu Ile Ser Leu Cys<br>                  285                    290                 295 | 1038 |
| tat cag tcc acc aca aac act cta act gtg gtt gtc tta aaa gct cga<br>Tyr Gln Ser Thr Thr Asn Thr Leu Thr Val Val Val Leu Lys Ala Arg<br>          300                    305                 310 | 1086 |
| cat ctg cct aaa tct gat gtg tcc gga ctt tca gat ccc tat gtc aaa<br>His Leu Pro Lys Ser Asp Val Ser Gly Leu Ser Asp Pro Tyr Val Lys<br>              315                    320                 325 | 1134 |
| gtg aac ctg tac cat gcc aaa aag aga atc tcc aag aag aag act cat<br>Val Asn Leu Tyr His Ala Lys Lys Arg Ile Ser Lys Lys Lys Thr His<br>          330                    335                 340 | 1182 |
| gtg aag aaa tgc acc ccc aat gca gtg ttc aat gag ctg ttt gtc ttt<br>Val Lys Lys Cys Thr Pro Asn Ala Val Phe Asn Glu Leu Phe Val Phe<br>345                    350                    355                 360 | 1230 |
| gat att cct tgt gag ggc ctt gaa gat ata agt gtt gaa ttt ttg gtt<br>Asp Ile Pro Cys Glu Gly Leu Glu Asp Ile Ser Val Glu Phe Leu Val<br>              365                    370                 375 | 1278 |

-continued

| | | |
|---|---|---|
| ttg gat tct gaa agg ggg tcc cga aat gag gta atc ggg cag tta gtc<br>Leu Asp Ser Glu Arg Gly Ser Arg Asn Glu Val Ile Gly Gln Leu Val<br>     380                             385                            390 | | 1326 |
| ttg ggt gca gca gca gaa gga act ggt gga gag cac tgg aaa gag atc<br>Leu Gly Ala Ala Ala Glu Gly Thr Gly Gly Glu His Trp Lys Glu Ile<br>     395                             400                            405 | | 1374 |
| tgt gac tac ccc agg aga caa att gcc aag tgg cac gtg ctc tgt gat<br>Cys Asp Tyr Pro Arg Arg Gln Ile Ala Lys Trp His Val Leu Cys Asp<br>     410                             415                            420 | | 1422 |
| ggt tagcatccta gccgtgagtt ggaacttaaa gttttttact aggcaaggag<br>Gly<br>425 | | 1475 |
| aaatttctt tctttctata ttggattgca agcttgggaa atcaagctac cttttttgttg | | 1535 |
| ttgttgttgt tgctagaaat ggattgaatt agtagaccag aaagtaactt caaatgtgta | | 1595 |
| ttatgataat ttccctatttt attagaagag ttggataaat tttcataaga tattcaatat | | 1655 |
| ctccttcaga ttaccagtga tataactagg aatagtcaga catttatga atactgtgcc | | 1715 |
| agaatcccaa attataaatg tgacaatctc attggaacat gtcacaaaaa gttaatgtga | | 1775 |
| ttaagattta aaaacgaaaa gtatgccttg ccttgtgaaa atttatccat ttatcttcag | | 1835 |
| gttgggggaa atcaattttt ctttaatcca aagatactaa aaaaatgtcc tccagtttgt | | 1895 |
| atttattaat tctgtcatgt gcaaatggtt gtcctgcata taaagtatc tggtcatttc | | 1955 |
| agtttggttt gtaattattt gatgcaattt tatcataaga gtaactcaga ttcatttcaa | | 2015 |
| aaggacagtg aacaagctga gaaattattt tatcaaaggg ctgagttgag aacactgtgg | | 2075 |
| ctgaaatata attttttctcc ccctaaggt tacatgtgag tcaaaatttt gtaaaatata | | 2135 |
| acctcacata agaaccatgg ccttggatta ttcactgcct gtcacaagcc tcagtgtggc | | 2195 |
| ctgagaaatc cctatgtacc tttgtgaaat tgttgaatta gttagtgaat aaagaaataa | | 2255 |
| acttcaacta gaaatccagt tagaagtgca attttcttat aggaaatagg tatagtgtgc | | 2315 |
| aagtgtactt ttaaggccat cgtttgtacc cagagtcggc atggccacct aagtcttcat | | 2375 |
| ttaatttatt gtcccccaga aaagattaag atgctacttg aaaagactgt gaagattttt | | 2435 |
| tacattgcca gataaaaagt gttacttaac caacaaacaa atgtaagact acaaaatcgt | | 2495 |
| tcaagagcaa ttctaatata atttacatat gttcacgcaa aatatgctta ggctgtcaaa | | 2555 |
| ttagcacaac aaagaatgtg tttcactatc ttttctaggc taatttgtct tgagctgttg | | 2615 |
| tctatagagc agtttacaga cttgtgtctt gtatcatttt ccagtgccag ggttctgaaa | | 2675 |
| ttcattcaga acctgttaga ttaaagctgc accctgtgat tatttgaaaa gaattagctt | | 2735 |
| gagagtaatg tcactatatt tgagttctta gagaagtatg agtggaactt gagtacagtt | | 2795 |
| gaattattaa atatgcaagt tagaaattaa gtctactgaa aaatttacat tttgagtcag | | 2855 |
| gttttgtgtc agtactttag cagtttttga gaatgtgttt gatatcacag tgtttgtaaa | | 2915 |
| ttctatgaaa aatgcatttt ccaaacaact tatacatgct ttttatgact atgcctaatg | | 2975 |
| taaagaaaat gtattacatt ctgtatgtac aaagattaaa atcaaccctc tttttttgtgc | | 3035 |
| tttaaaatga ctttgggatt aaaaaagcat atttcccaat cattgtcttc attccactac | | 3095 |
| aaagtcacct cacagcatct tgctccactc ggcatctctg tgaaagcaac atgaaatgaa | | 3155 |
| ctgtagtagg tgtgtagttt ggggaagtca aatggccatt ttatgtatgt gcatttggta | | 3215 |
| tcatgggccg tggaacagaa tatatgttgg acctctgaaa agttgtaagg ggccaaatct | | 3275 |
| aagtattctt cacggcagcc agaagttaat ggtggtagca gctgaggtat ggttgttgga | | 3335 |
| cgaggccgat ttttttttttt taacatggaa caatgaaacc aacaacaaac attttttaaaa | | 3395 |

-continued

```
ttaaaatgga taatttgtaa atagttttta gcttttaaaa tttaaagtgt ttttgagtgt    3455
gaaaagttga gtaaaactat ttgcaactgg ttttcagaaa agagaaaaga aacaacaaag    3515
gaattgaaac aggcagggag atcttaatac ctaatttcat catttctgca aaatgtactg    3575
ttttagaatg tattacaata tcaatgtgaa tatcttgaat cctgttacaa atcctgcact    3635
gtattaaaca tgtaaattaa ttgtttgtct gattagccaa tctcaccacc caaatgggga    3695
ggtatacatg tttgaagaac gtgtaactcg gtaattgatt tgttctgatg ttgtaactca    3755
atagaagtgt tttggaagga agcatggtgt gtgagacagt gtctgttctt ttgtgccagc    3815
tctgtatgat gtttgtaaga ccatgtttgt aagacatgaa taaattgctg cttttgccca    3875
aaaaaaaaaa aaaaa                                                     3891
```

```
<210> SEQ ID NO 2
<211> LENGTH: 425
<212> TYPE: PRT
<213> ORGANISM: Homo sapiens
<220> FEATURE:
<223> OTHER INFORMATION: product = Repro-PC-1.0

<400> SEQUENCE: 2

Met Ala Pro Ile Thr Thr Ser Arg Glu Glu Phe Asp Glu Ile Pro Thr
 1               5                   10                  15

Val Val Gly Ile Phe Ser Ala Phe Gly Leu Val Phe Thr Val Ser Leu
                20                  25                  30

Phe Ala Trp Ile Cys Cys Gln Arg Lys Ser Ser Lys Ser Asn Lys Thr
            35                  40                  45

Pro Pro Tyr Lys Phe Val His Val Leu Lys Gly Val Asp Ile Tyr Pro
        50                  55                  60

Glu Asn Leu Asn Ser Lys Lys Phe Gly Ala Asp Asp Lys Asn Glu
65                  70                  75                  80

Val Lys Asn Lys Pro Ala Val Pro Lys Asn Ser Leu His Leu Asp Leu
                85                  90                  95

Glu Lys Arg Asp Leu Asn Gly Asn Phe Pro Lys Thr Asn Leu Lys Pro
            100                 105                 110

Gly Ser Pro Ser Asp Leu Glu Asn Ala Thr Pro Lys Leu Phe Leu Glu
        115                 120                 125

Gly Glu Lys Glu Ser Val Ser Pro Glu Ser Leu Lys Ser Ser Thr Ser
    130                 135                 140

Leu Thr Ser Glu Glu Lys Gln Glu Lys Leu Gly Thr Leu Phe Phe Ser
145                 150                 155                 160

Leu Glu Tyr Asn Phe Glu Arg Lys Ala Phe Val Val Asn Ile Lys Glu
                165                 170                 175

Ala Arg Gly Leu Pro Ala Met Asp Glu Gln Ser Met Thr Ser Asp Pro
            180                 185                 190

Tyr Ile Lys Met Thr Ile Leu Pro Glu Lys Lys His Lys Val Lys Thr
        195                 200                 205

Arg Val Leu Arg Lys Thr Leu Asp Pro Ala Phe Asp Glu Thr Phe Thr
    210                 215                 220

Phe Tyr Gly Ile Pro Tyr Thr Gln Ile Gln Glu Leu Ala Leu His Phe
225                 230                 235                 240

Thr Ile Leu Ser Phe Asp Arg Phe Ser Arg Asp Asp Ile Ile Gly Glu
                245                 250                 255

Val Leu Ile Pro Leu Ser Gly Ile Glu Leu Ser Glu Gly Lys Met Leu
            260                 265                 270
```

-continued

```
Met Asn Arg Glu Ile Ile Lys Arg Asn Val Arg Lys Ser Ser Gly Arg
            275                 280                 285
Gly Glu Leu Leu Ile Ser Leu Cys Tyr Gln Ser Thr Thr Asn Thr Leu
        290                 295                 300
Thr Val Val Val Leu Lys Ala Arg His Leu Pro Lys Ser Asp Val Ser
305                 310                 315                 320
Gly Leu Ser Asp Pro Tyr Val Lys Val Asn Leu Tyr His Ala Lys Lys
                325                 330                 335
Arg Ile Ser Lys Lys Lys Thr His Val Lys Lys Cys Thr Pro Asn Ala
            340                 345                 350
Val Phe Asn Glu Leu Phe Val Phe Asp Ile Pro Cys Glu Gly Leu Glu
        355                 360                 365
Asp Ile Ser Val Glu Phe Leu Val Leu Asp Ser Glu Arg Gly Ser Arg
    370                 375                 380
Asn Glu Val Ile Gly Gln Leu Val Leu Gly Ala Ala Ala Glu Gly Thr
385                 390                 395                 400
Gly Gly Glu His Trp Lys Glu Ile Cys Asp Tyr Pro Arg Arg Gln Ile
                405                 410                 415
Ala Lys Trp His Val Leu Cys Asp Gly
            420                 425

<210> SEQ ID NO 3
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: 5' oligo (109) Upper Primer

<400> SEQUENCE: 3
cagttttccc ttcagcacct c                                           21

<210> SEQ ID NO 4
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: 3' oligo (3489) Lower Primer

<400> SEQUENCE: 4
ttcctttgtt gtttcttttc tcttttctga                                  30

<210> SEQ ID NO 5
<211> LENGTH: 425
<212> TYPE: PRT
<213> ORGANISM: rat
<220> FEATURE:
<223> OTHER INFORMATION: residues 1-425 = rat synaptotagmin 4 (SYT4)

<400> SEQUENCE: 5

Met Ala Pro Ile Thr Thr Ser Arg Val Glu Phe Asp Glu Ile Pro Thr
1               5                   10                  15
Val Val Gly Ile Phe Ser Ala Phe Gly Leu Val Phe Thr Val Ser Leu
            20                  25                  30
Phe Ala Trp Ile Cys Cys Gln Arg Arg Ser Ala Lys Ser Asn Lys Thr
        35                  40                  45
Pro Pro Tyr Lys Phe Val His Val Leu Lys Gly Val Asp Ile Tyr Pro
```

```
            50                  55                  60
Glu Asn Leu Ser Ser Lys Lys Phe Gly Gly Asp Asp Lys Ser Glu
65                  70                  75                  80

Ala Lys Arg Lys Ala Ala Leu Pro Asn Leu Ser Leu His Leu Asp Leu
                85                  90                  95

Glu Lys Arg Asp Leu Asn Gly Asn Phe Pro Lys Thr Asn Pro Lys Ala
            100                 105                 110

Gly Ser Ser Ser Asp Leu Glu Asn Val Thr Pro Lys Leu Phe Pro Glu
            115                 120                 125

Thr Glu Lys Glu Ala Val Ser Pro Glu Ser Leu Lys Ser Ser Thr Ser
130                 135                 140

Leu Thr Ser Glu Glu Lys Gln Glu Lys Leu Gly Thr Leu Phe Leu Ser
145                 150                 155                 160

Leu Glu Tyr Asn Phe Glu Lys Lys Ala Phe Val Val Asn Ile Lys Glu
                165                 170                 175

Ala Gln Gly Leu Pro Ala Met Asp Glu Gln Ser Met Thr Ser Asp Pro
            180                 185                 190

Tyr Ile Lys Met Thr Ile Leu Pro Glu Lys Lys His Lys Val Lys Thr
            195                 200                 205

Arg Val Leu Arg Lys Thr Leu Asp Pro Val Phe Asp Glu Thr Phe Thr
210                 215                 220

Phe Tyr Gly Val Pro Tyr Pro His Ile Gln Glu Leu Ser Leu His Phe
225                 230                 235                 240

Thr Val Leu Ser Phe Asp Arg Phe Ser Arg Asp Asp Val Ile Gly Glu
                245                 250                 255

Val Leu Val Pro Leu Ser Gly Ile Glu Leu Ser Asp Gly Lys Met Leu
            260                 265                 270

Met Thr Arg Glu Ile Ile Lys Arg Asn Ala Lys Lys Ser Ser Gly Arg
            275                 280                 285

Gly Glu Leu Leu Val Ser Leu Cys Tyr Gln Ser Thr Thr Asn Thr Leu
            290                 295                 300

Thr Val Val Val Leu Lys Ala Arg His Leu Pro Lys Ser Asp Val Ser
305                 310                 315                 320

Gly Leu Ser Asp Pro Tyr Val Lys Val Asn Leu Tyr His Ala Lys Lys
                325                 330                 335

Arg Ile Ser Lys Lys Lys Thr His Val Lys Lys Cys Thr Pro Asn Ala
            340                 345                 350

Val Phe Asn Glu Leu Phe Val Phe Asp Ile Pro Cys Glu Ser Leu Glu
            355                 360                 365

Glu Ile Ser Val Glu Phe Leu Val Leu Asp Ser Glu Arg Gly Ser Arg
            370                 375                 380

Asn Glu Val Ile Gly Arg Leu Val Leu Gly Ala Thr Ala Glu Gly Ser
385                 390                 395                 400

Gly Gly Gly His Trp Lys Glu Ile Cys Asp Phe Pro Arg Arg Gln Ile
                405                 410                 415

Ala Lys Trp His Met Leu Cys Asp Gly
            420                 425

<210> SEQ ID NO 6
<211> LENGTH: 117
<212> TYPE: PRT
<213> ORGANISM: Homo sapiens
<220> FEATURE:
<221> NAME/KEY: PEPTIDE
<222> LOCATION: (1)..(117)
```

-continued

<223> OTHER INFORMATION: PKC-C2 internal repeat (amino acid positions
      154-271)

<400> SEQUENCE: 6

Glu Asn Val Pro Ser Leu Cys Gly Cys Asp His Thr Glu Arg Arg Gly
 1               5                  10                  15

Arg Ile Tyr Leu Glu Ile Asn Val Lys Glu Asn Leu Leu Thr Val Gln
            20                  25                  30

Ile Lys Glu Gly Arg Asn Leu Ile Pro Met Asp Pro Asn Gly Leu Ser
        35                  40                  45

Asp Pro Tyr Val Lys Val Lys Leu Ile Pro Asp Lys Asp Gln Ser
    50                  55                  60

Lys Lys Lys Thr Arg Thr Thr Lys Ala Cys Leu Asn Pro Val Trp Asn
65                  70                  75                  80

Glu Thr Leu Thr Tyr Asp Leu Lys Pro Glu Asp Lys Asp Arg Arg Ile
                85                  90                  95

Leu Ile Glu Val Trp Asp Trp Asp Arg Thr Ser Arg Asn Asp Phe Met
            100                 105                 110

Gly Ala Leu Ser Phe
        115

<210> SEQ ID NO 7
<211> LENGTH: 121
<212> TYPE: PRT
<213> ORGANISM: Homo sapiens
<220> FEATURE:
<221> NAME/KEY: PEPTIDE
<222> LOCATION: (1)..(121)
<223> OTHER INFORMATION: Repro-PC-1.0 (PC-20) "B" internal repeat (amino
      acid) positions 276-397

<400> SEQUENCE: 7

Glu Ile Ile Lys Arg Asn Val Arg Lys Ser Ser Gly Arg Gly Glu Leu
 1               5                  10                  15

Leu Ile Ser Leu Cys Tyr Gln Ser Thr Ile Asn Thr Leu Thr Val Val
            20                  25                  30

Val Leu Lys Ala Arg His Leu Pro Lys Ser Asp Val Ser Gly Leu Ser
        35                  40                  45

Asp Pro Tyr Val Lys Val Asn Leu Tyr His Ala Lys Lys Arg Ile Ser
    50                  55                  60

Lys Lys Lys Thr His Val Lys Lys Cys Thr Pro Asn Ala Val Phe Asn
65                  70                  75                  80

Glu Leu Phe Val Phe Asp Ile Pro Cys Glu Gly Leu Glu Asp Ile Ser
                85                  90                  95

Val Glu Phe Leu Val Leu Asp Ser Glu Arg Gly Ser Arg Asn Glu Val
            100                 105                 110

Ile Gly Gln Leu Val Leu Gly Ala Ala
        115                 120

<210> SEQ ID NO 8
<211> LENGTH: 115
<212> TYPE: PRT
<213> ORGANISM: rat
<220> FEATURE:
<221> NAME/KEY: PEPTIDE
<222> LOCATION: (1)..(115)
<223> OTHER INFORMATION: synaptotagmin "B" internal repeat (amino acid
      positions 268-383)

<400> SEQUENCE: 8

Lys Glu Glu Gln Glu Lys Leu Gly Asp Ile Cys Phe Ser Leu Arg Tyr
1               5                   10                  15

Val Pro Thr Ala Gly Lys Leu Thr Val Val Ile Leu Glu Ala Lys Asn
                20                  25                  30

Leu Lys Lys Met Asp Val Gly Gly Leu Ser Asp Pro Tyr Val Lys Ile
            35                  40                  45

His Leu Met Gln Asn Gly Lys Arg Leu Lys Lys Lys Thr Thr Ile
        50                  55                  60

Lys Lys Asn Thr Leu Asn Pro Tyr Tyr Asn Glu Ser Phe Ser Phe Glu
65              70                  75                  80

Val Pro Phe Glu Gln Ile Gln Lys Val Gln Val Val Thr Val Leu
                85                  90                  95

Asp Tyr Asp Lys Ile Gly Lys Asn Asp Ala Ile Gly Lys Val Phe Val
            100                 105                 110

Gly Tyr Asn
        115

<210> SEQ ID NO 9
<211> LENGTH: 120
<212> TYPE: PRT
<213> ORGANISM: rat
<220> FEATURE:
<221> NAME/KEY: PEPTIDE
<222> LOCATION: (1)..(120)
<223> OTHER INFORMATION: synaptotagmin "A" internal repeat (amino acid
      positions 134-254)

<400> SEQUENCE: 9

Lys Glu Glu Pro Lys Glu Glu Lys Leu Gly Lys Leu Gln Tyr Ser
1               5                   10                  15

Leu Asp Tyr Asp Phe Gln Asn Asn Gln Leu Leu Val Gly Ile Ile Gln
                20                  25                  30

Ala Ala Glu Leu Pro Ala Leu Asp Met Gly Gly Thr Ser Asp Pro Tyr
            35                  40                  45

Val Lys Val Phe Leu Leu Pro Asp Lys Lys Lys Phe Glu Thr Lys
50                  55                  60

Val His Arg Lys Thr Leu Asn Pro Val Phe Asn Glu Gln Phe Thr Phe
65              70                  75                  80

Lys Val Pro Tyr Ser Glu Leu Gly Gly Lys Thr Leu Val Met Ala Val
                85                  90                  95

Tyr Asp Phe Asp Arg Phe Ser Lys His Asp Ile Ile Gly Glu Phe Lys
            100                 105                 110

Val Pro Met Asn Thr Val Asp Phe
        115                 120

<210> SEQ ID NO 10
<211> LENGTH: 113
<212> TYPE: PRT
<213> ORGANISM: Homo sapiens
<220> FEATURE:
<221> NAME/KEY: PEPTIDE
<222> LOCATION: (1)..(113)
<223> OTHER INFORMATION: Repro=PC-1.0 (PC-20) "A" internal repeat amino
      acid positions 150-263)

<400> SEQUENCE: 10

Lys Gln Glu Lys Leu Gly Thr Leu Phe Phe Ser Leu Glu Tyr Asn Phe
1               5                   10                  15

Glu Arg Lys Ala Phe Val Val Asn Ile Lys Glu Ala Arg Gly Leu Pro
                20                  25                  30

Ala Met Asp Glu Gln Ser Met Thr Ser Asp Pro Tyr Ile Lys Met Thr
            35                  40                  45

Ile Leu Pro Glu Lys Lys His Lys Val Lys Thr Arg Val Leu Arg Lys
 50                  55                  60

Thr Leu Asp Pro Ala Phe Asp Glu Thr Phe Thr Phe Tyr Gly Ile Pro
 65                  70                  75                  80

Tyr Thr Gln Ile Gln Glu Leu Ala Leu His Phe Thr Ile Leu Ser Phe
                 85                  90                  95

Asp Arg Phe Ser Arg Asp Asp Ile Ile Gly Glu Val Leu Ile Pro Leu
                100                 105                 110

Ser

<210> SEQ ID NO 11
<211> LENGTH: 9
<212> TYPE: PRT
<213> ORGANISM: Homo sapiens
<220> FEATURE:
<221> NAME/KEY: Modified-site
<220> FEATURE:
<222> LOCATION: 1
<220> FEATURE:
<223> OTHER INFORMATION: Xaa=Thr, Ser or Met
<220> FEATURE:
<221> NAME/KEY: Modified-site
<220> FEATURE:
<222> LOCATION: 2
<220> FEATURE:
<223> OTHER INFORMATION: Xaa=Asp, Glu, Ala, Ser or Thr
<220> FEATURE:
<221> NAME/KEY: Modified-site
<220> FEATURE:
<222> LOCATION: 3-8
<220> FEATURE:
<223> OTHER INFORMATION: Xaa=Any natural or synthetic amino acid

<400> SEQUENCE: 11

Xaa Xaa Xaa Xaa Xaa Xaa Xaa Xaa Tyr
 1               5

<210> SEQ ID NO 12
<211> LENGTH: 10
<212> TYPE: PRT
<213> ORGANISM: Homo sapiens
<220> FEATURE:
<221> NAME/KEY: Modified-site
<220> FEATURE:
<222> LOCATION: 1
<220> FEATURE:
<223> OTHER INFORMATION: Xaa=Thr, Ser or Met
<220> FEATURE:
<221> NAME/KEY: Modified-site
<220> FEATURE:
<222> LOCATION: 2
<220> FEATURE:
<223> OTHER INFORMATION: Xaa=Asp, Glu, Ala, Ser or Thr
<220> FEATURE:
<221> NAME/KEY: Modified-site
<220> FEATURE:
<222> LOCATION: 3-9
<220> FEATURE:
<223> OTHER INFORMATION: Xaa=Any natural or synthetic amino acid

<400> SEQUENCE: 12

Xaa Xaa Xaa Xaa Xaa Xaa Xaa Xaa Xaa Tyr
 1               5                  10

<210> SEQ ID NO 13
<211> LENGTH: 7

```
<212> TYPE: PRT
<213> ORGANISM: Homo sapiens
<220> FEATURE:
<221> NAME/KEY: Modified-site
<220> FEATURE:
<222> LOCATION: 1
<220> FEATURE:
<223> OTHER INFORMATION: Xaa=Glu or Asp
<220> FEATURE:
<221> NAME/KEY: Modified-site
<220> FEATURE:
<222> LOCATION: 2-6
<220> FEATURE:
<223> OTHER INFORMATION: Xaa=Any natural or synthetic amino acid

<400> SEQUENCE: 13

Xaa Xaa Xaa Xaa Xaa Xaa Tyr
  1               5

<210> SEQ ID NO 14
<211> LENGTH: 8
<212> TYPE: PRT
<213> ORGANISM: Homo sapiens
<220> FEATURE:
<221> NAME/KEY: Modified-site
<220> FEATURE:
<222> LOCATION: 1
<220> FEATURE:
<223> OTHER INFORMATION: Xaa=Glu or Asp
<220> FEATURE:
<221> NAME/KEY: Modified-site
<220> FEATURE:
<222> LOCATION: 2-7
<220> FEATURE:
<223> OTHER INFORMATION: Xaa=Any natural or synthetic amino acid

<400> SEQUENCE: 14

Xaa Xaa Xaa Xaa Xaa Xaa Xaa Tyr
  1               5

<210> SEQ ID NO 15
<211> LENGTH: 9
<212> TYPE: PRT
<213> ORGANISM: Homo sapiens
<220> FEATURE:
<221> NAME/KEY: Modified-site
<220> FEATURE:
<222> LOCATION: 1
<220> FEATURE:
<223> OTHER INFORMATION: Xaa=Any natural or synthetic amino acid
<220> FEATURE:
<221> NAME/KEY: Modified-site
<220> FEATURE:
<222> LOCATION: 2
<220> FEATURE:
<223> OTHER INFORMATION: Xaa=Leu, Met, Ile, Val, Ser, Ala, Thr, Phe,
      Cys, Gly, Asp or Glu
<220> FEATURE:
<221> NAME/KEY: Modified-site
<220> FEATURE:
<222> LOCATION: 3-8
<220> FEATURE:
<223> OTHER INFORMATION: Xaa=Any natural or synthetic amino acid
<220> FEATURE:
<221> NAME/KEY: Modified-site
<220> FEATURE:
<222> LOCATION: 9
<220> FEATURE:
<223> OTHER INFORMATION: Xaa=Lys, Arg or Tyr

<400> SEQUENCE: 15

Xaa Xaa Xaa Xaa Xaa Xaa Xaa Xaa Xaa
  1               5
```

```
<210> SEQ ID NO 16
<211> LENGTH: 10
<212> TYPE: PRT
<213> ORGANISM: Homo sapiens
<220> FEATURE:
<221> NAME/KEY: Modified-site
<220> FEATURE:
<222> LOCATION: 1
<220> FEATURE:
<223> OTHER INFORMATION: Xaa=Any natural or synthetic amino acid
<220> FEATURE:
<221> NAME/KEY: Modified-site
<220> FEATURE:
<222> LOCATION: 2
<220> FEATURE:
<223> OTHER INFORMATION: Xaa= Leu, Met, Ile, Val, Ser, Ala, Thr, Phe,
      Cys, Gly, Asp or Glu
<220> FEATURE:
<221> NAME/KEY: Modified-site
<220> FEATURE:
<222> LOCATION: 3-9
<220> FEATURE:
<223> OTHER INFORMATION: Xaa=Any natural or synthetic amino acid
<220> FEATURE:
<221> NAME/KEY: Modified-site
<220> FEATURE:
<222> LOCATION: 10
<220> FEATURE:
<223> OTHER INFORMATION: Xaa=Lys, Arg or Tyr

<400> SEQUENCE: 16

Xaa Xaa Xaa Xaa Xaa Xaa Xaa Xaa Xaa Xaa
 1               5                  10

<210> SEQ ID NO 17
<211> LENGTH: 9
<212> TYPE: PRT
<213> ORGANISM: Homo sapiens
<220> FEATURE:
<221> NAME/KEY: Modified-site
<220> FEATURE:
<222> LOCATION: 1
<220> FEATURE:
<223> OTHER INFORMATION: Xaa=Any natural or synthetic amino acid
<220> FEATURE:
<221> NAME/KEY: Modified-site
<220> FEATURE:
<222> LOCATION: 2
<220> FEATURE:
<223> OTHER INFORMATION: Xaa=Thr or Val
<220> FEATURE:
<221> NAME/KEY: Modified-site
<220> FEATURE:
<222> LOCATION: 3-8
<220> FEATURE:
<223> OTHER INFORMATION: Xaa=Any natural or synthetic amino acid

<400> SEQUENCE: 17

Xaa Xaa Xaa Xaa Xaa Xaa Xaa Xaa Lys
 1               5

<210> SEQ ID NO 18
<211> LENGTH: 10
<212> TYPE: PRT
<213> ORGANISM: Homo sapiens
<220> FEATURE:
<221> NAME/KEY: Modified-site
<220> FEATURE:
<222> LOCATION: 1
<220> FEATURE:
<223> OTHER INFORMATION: Xaa=Any natural or synthetic amino acid
<220> FEATURE:
<221> NAME/KEY: Modified-site
<220> FEATURE:
```

```
<222> LOCATION: 2
<220> FEATURE:
<223> OTHER INFORMATION: Xaa=Thr or Val
<220> FEATURE:
<221> NAME/KEY: Modified-site
<220> FEATURE:
<222> LOCATION: 3-9
<220> FEATURE:
<223> OTHER INFORMATION: Xaa=Any natural or synthetic amino acid

<400> SEQUENCE: 18

Xaa Xaa Xaa Xaa Xaa Xaa Xaa Xaa Xaa Lys
 1               5                  10

<210> SEQ ID NO 19
<211> LENGTH: 9
<212> TYPE: PRT
<213> ORGANISM: Homo sapiens
<220> FEATURE:
<221> NAME/KEY: Modified-site
<220> FEATURE:
<222> LOCATION: 1
<220> FEATURE:
<223> OTHER INFORMATION: Xaa=Any natural or synthetic amino acid
<220> FEATURE:
<221> NAME/KEY: Modified-site
<220> FEATURE:
<222> LOCATION: 2
<220> FEATURE:
<223> OTHER INFORMATION: Xaa=Tyr, Phe or Trp
<220> FEATURE:
<221> NAME/KEY: Modified-site
<220> FEATURE:
<222> LOCATION: 3-8
<220> FEATURE:
<223> OTHER INFORMATION: Xaa=Any natural or synthetic amino acid
<220> FEATURE:
<221> NAME/KEY: Modified-site
<220> FEATURE:
<222> LOCATION: 9
<220> FEATURE:
<223> OTHER INFORMATION: Xaa=Phe, Ile, Trp, Met or Leu

<400> SEQUENCE: 19

Xaa Xaa Xaa Xaa Xaa Xaa Xaa Xaa Xaa
 1               5

<210> SEQ ID NO 20
<211> LENGTH: 10
<212> TYPE: PRT
<213> ORGANISM: Homo sapiens
<220> FEATURE:
<221> NAME/KEY: Modified-site
<220> FEATURE:
<222> LOCATION: 1
<220> FEATURE:
<223> OTHER INFORMATION: Xaa=Any natural or synthetic amino acid
<220> FEATURE:
<221> NAME/KEY: Modified-site
<220> FEATURE:
<222> LOCATION: 2
<220> FEATURE:
<223> OTHER INFORMATION: Xaa=Tyr, Phe or Trp
<220> FEATURE:
<221> NAME/KEY: Modified-site
<220> FEATURE:
<222> LOCATION: 3-10
<220> FEATURE:
<223> OTHER INFORMATION: Xaa=Any natural or synthetic amino acid

<400> SEQUENCE: 20

Xaa Xaa Xaa Xaa Xaa Xaa Xaa Xaa Xaa Xaa
 1               5                  10
```

<210> SEQ ID NO 21
<211> LENGTH: 31
<212> TYPE: PRT
<213> ORGANISM: Homo sapiens

<400> SEQUENCE: 21

Glu Glu Phe Asp Glu Ile Pro Thr Val Val Gly Ile Phe Ser Ala Phe
 1               5                  10                  15

Gly Leu Val Phe Thr Val Ser Leu Phe Ala Trp Ile Cys Cys Gln
            20                  25                  30

<210> SEQ ID NO 22
<211> LENGTH: 34
<212> TYPE: PRT
<213> ORGANISM: Homo sapiens

<400> SEQUENCE: 22

Ser Ser Lys Ser Asn Lys Thr Pro Pro Tyr Lys Phe Val His Val Leu
 1               5                  10                  15

Lys Gly Val Asp Ile Tyr Pro Glu Asn Leu Asn Ser Lys Lys Lys Phe
            20                  25                  30

Gly Ala

<210> SEQ ID NO 23
<211> LENGTH: 25
<212> TYPE: PRT
<213> ORGANISM: Homo sapiens

<400> SEQUENCE: 23

Ser Pro Ser Asp Leu Glu Asn Ala Thr Pro Lys Leu Phe Leu Glu Gly
 1               5                  10                  15

Glu Lys Glu Ser Val Ser Pro Glu Ser
            20                  25

<210> SEQ ID NO 24
<211> LENGTH: 60
<212> TYPE: PRT
<213> ORGANISM: Homo sapiens

<400> SEQUENCE: 24

Leu Pro Glu Lys Lys His Lys Val Lys Thr Arg Val Leu Arg Lys Thr
 1               5                  10                  15

Leu Asp Pro Ala Phe Asp Glu Thr Phe Thr Phe Tyr Gly Ile Pro Tyr
            20                  25                  30

Thr Gln Ile Gln Glu Leu Ala Leu His Phe Thr Ile Leu Ser Phe Asp
        35                  40                  45

Arg Phe Ser Arg Asp Asp Ile Ile Gly Glu Val Leu
    50                  55                  60

<210> SEQ ID NO 25
<211> LENGTH: 46
<212> TYPE: PRT
<213> ORGANISM: Homo sapiens

<400> SEQUENCE: 25

Ile Pro Leu Ser Gly Ile Glu Leu Ser Glu Gly Lys Met Leu Met Asn
 1               5                  10                  15

Arg Glu Ile Ile Lys Arg Asn Val Arg Lys Ser Ser Gly Arg Gly Glu
            20                  25                  30

-continued

```
Leu Leu Ile Ser Leu Cys Tyr Gln Ser Thr Thr Asn Thr Leu
        35                  40                  45

<210> SEQ ID NO 26
<211> LENGTH: 32
<212> TYPE: PRT
<213> ORGANISM: Homo sapiens

<400> SEQUENCE: 26

Val Leu Asp Ser Glu Arg Gly Ser Arg Asn Glu Val Ile Gly Gln Leu
 1               5                  10                  15

Val Leu Gly Ala Ala Glu Gly Thr Gly Gly Glu His Trp Lys Glu
            20                  25                  30

<210> SEQ ID NO 27
<211> LENGTH: 6
<212> TYPE: PRT
<213> ORGANISM: Homo sapiens
<220> FEATURE:
<221> NAME/KEY: Modified-site
<220> FEATURE:
<222> LOCATION: 5
<220> FEATURE:
<223> OTHER INFORMATION: Xaa=Val or Ile

<400> SEQUENCE: 27

Ser Asp Pro Tyr Xaa Lys
 1               5
```

PROSTATE CANCER-SPECIFIC MARKER

REFERENCE TO RELATED APPLICATION

This application claims the benefit of the priority date of U.S. provisional patent application 60/041,246, filed Mar. 7, 1997, and provisional patent application 60/047,811, filed May 15, 1997, incorporated herein by reference in their entirety.

The present application is a Continuation Patent Application of U.S. patent application Ser. No. 09/036,315 filed Mar. 6, 1998 and Divisional patent application Ser. No. 09/535,597 filed Mar. 27, 2000.

FIELD OF THE INVENTION

The present invention provides polynucleotides encoding a prostate cancer-specific cDNA, proteins encoded by the polynucleotides, and methods of using these materials.

BACKGROUND OF THE INVENTION

The prostate is almost invariably the site of benign and malignant proliferative changes in aging males. Benign prostatic hypertrophy (BPH) is the most common non-malignant proliferative abnormality of internal organs. A high percentage of these age-related growth disorders develop into malignancies. As a result of this, adenocarcinoma of the prostate represents the most common malignancy in American males and is the second leading cause of cancer deaths in men.

A useful method in the diagnosis of prostate cancer is determining the level of prostate specific antigen (PSA) in the blood. PSA is a glycoprotein secreted by the prostate gland. However, the PSA test has limitations of sensitivity and selectivity: In general, levels above 4 ng/ml are suggestive of cancer and levels above 10 ng/ml are highly suggestive. However, many individuals with elevated levels do not have prostate cancer, but exhibit benign prostatic hypertrophy. Conversely, many persons with prostate cancer have normal PSA levels at the time of diagnosis. Therefore, prostate cancer markers with greater sensitivity and selectivity for prostate cancer would be useful for, among other things, the diagnosis of prostate cancer.

SUMMARY OF THE INVENTION

A cDNA encoding a prostate cancer-specific marker, called Repro-PC-1.0, has been cloned and its nucleotide sequence determined. The nucleotide sequence of the cDNA and deduced amino acid sequence of Repro-PC-1.0 are presented as SEQ ID NO:1 and SEQ ID NO:2, respectively. Repro-PC-1.0 is expressed in prostate cancer cells and is useful as a marker in the detection of prostate cancer. Inhibition of Repro-PC-1.0 expression is useful in the prophylactic and therapeutic treatment of prostate cancer.

It also has been found that Repro-PC-1.0 expression is dependent on environment—cells from the prostate adenocarcinoma cell line, LNCaP, over-expresses Repro-PC-1.0 when propagated in male nude mice, but not when propagated in female nude mice. Repro-PC-1.0 has a significant level of amino acid sequence identity with the synaptotagmins. Therefore, it is believed that Repro-PC-1.0 functions in membrane fusion and membrane budding reactions.

Accordingly, the invention provides recombinant polynucleotide molecules comprising a nucleotide sequence encoding Repro-PC-1.0 polypeptide or Repro-PC1.0. Repro-PC-1.0 peptides include native Repro-PC-1.0 (SEQ ID NO:2) and allelic variants of it. Repro-PC-1.0 analogs include active analogs, which have the biological activity of Repro-PC-1.0, inactive analogs, useful as decoys, and immunogenic analogs, that, when used as an immunogen, elicit an immune response against Repro-PC-1.0 or cells expressing it. In one embodiment, the recombinant polynucleotide molecule comprises a nucleotide sequence encoding at least 5 consecutive amino acids of Repro-PC-1.0 polypeptide (SEQ ID NO: 1). In another embodiment the nucleotide sequence is substantially identical or identical to the nucleotide sequence of Repro-PC-1.0 (SEQ ID NO: 1).

In one aspect this invention provides expression vectors comprising expression control sequences operatively linked to a nucleotide sequence encoding a Repro-PC-1.0 protein or an Repro-PC-1.0 analog.

In another aspect, this invention provides polynucleotide probes and primers of at least 7 nucleotides that specifically hybridize to a sequence selected from Repro-PC-1.0 cDNA (SEQ ID NO: 1) or its complement.

In another aspect, this invention provides an inhibitory polynucleotide comprising an antisense sequence of at least 7 nucleotides that specifically hybridizes to a nucleotide sequence selected from Repro-PC-1.0 cDNA (SEQ ID NO: 1) and that inhibits expression of Repro-PC-1.0 in cells.

In another aspect, this invention provides expression vectors comprising expression control sequences operably linked to a nucleotide sequence encoding Repro-PC-1.0 polypeptide, a Repro-PC-1.0 analog or a probe, primer or inhibitory polynucleotide of this invention.

In another aspect this invention provides recombinant cells into which have been introduced an expression vector comprising expression control sequences operatively linked to a nucleotide sequence encoding a Repro-PC-1.0 polypeptide or a Repro-PC-1.0 analog.

In another aspect, this invention provides a method for expressing Repro-PC-1.0 mRNA in a cell that has a nucleotide sequence encoding Repro-PC-1.0 comprising operably linking an expression control sequence to the nucleotide sequence. The nucleotide sequence can be, for example, a sequence within the animal's genomic DNA.

In another aspect, this invention provides methods for producing a Repro-PC-1.0 polypeptide or a Repro-PC-1.0 analog comprising culturing a recombinant cell that comprises a recombinant polynucleotide that comprises expression control sequences operably linked to a nucleotide sequence encoding the Repro-PC-1.0 polypeptide or Repro-PC-1.0 analog.

In another aspect, this invention provides methods for detecting a Repro-PC-1.0 polynucleotide in a sample, comprising the steps of (a) contacting the sample with a polynucleotide probe or primer comprising a sequence of at least 7 nucleotides that specifically hybridizes to a nucleotide sequence selected from Repro-PC-1.0 and (b) detecting whether the polynucleotide has specifically hybridized to the Repro-PC-1.0 polynucleotide. Specific hybridization provides a detection of Repro-PC-1.0 in the sample.

In another aspect this invention provides methods for inhibiting Repro-PC-1.0 expression in a cell comprising providing the cell with an inhibitory polynucleotide of the invention or with a polynucleotide that encodes an inactive decoy Repro-PC-1.0 analog.

In another aspect this invention provides purified, recombinant Repro-PC-1.0 protein, e.g. a protein whose amino acid sequence is identical to the sequence of SEQ ID NO:2 and allelic variants of it. The invention also provides Repro-PC-1.0 analogs whose amino acid sequence is not naturally occurring and is substantially identical to the amino acid sequence of Repro-PC-1.0 (SEQ ID NO:2). Such analogs include active analogs having the biological activity of Repro-PC-1.0, as well as immunogenic analogs, capable of eliciting the production of antibodies that recognize Repro-PC-1.0.

In another aspect, this invention provides antibodies that specifically bind to Repro-PC-1.0 polypeptide.

In another aspect, this invention provides methods for detecting a Repro-PC-1.0 polypeptide in a sample, comprising the steps of (a) contacting the sample with an antibody that specifically binds to the Repro-PC-1.0 polypeptide and (b) detecting specific binding between the antibody and Repro-PC-1.0 polypeptide. Specific binding provides a detection of Repro-PC-1.0 in the sample.

In another aspect, this invention provides methods for diagnosing, monitoring or making a prognosis for prostate cancer in a subject. The methods involve detecting Repro-PC-1.0 mRNA or polypeptide in a sample from the subject. In the diagnostic method, a diagnostic amount of Repro-PC-1.0 mRNA or Repro-PC-1.0 polypeptide in a sample from the subject is determined and the diagnostic amount is compared with a normal range of Repro-PC-1.0 mRNA or Repro-PC-1.0 polypeptide in a non-cancerous control sample. A diagnostic amount above the normal range provides a positive indication in the diagnosis of prostate cancer. The detection of an amount of Repro-PC-1.0 mRNA or polypeptide at a particular prognostic level provides a prognosis for the subject. Methods for monitoring the progress of prostate cancer involve detecting the amount of Repro-PC-1.0 mRNA or Repro-PC-1.0 polypeptide in the subject at a first and a second time, and comparing the amounts. A change in the amount indicates a change in the course of the disease, with a decreasing amount indicating remission of prostate cancer and increase indicating progression of the prostate cancer. One embodiment of these methods involves diagnostic imaging of Repro-PC-1.0 in the body using detectably labeled probes, primers or antibodies. Methods for making a prognosis for prostate cancer in a subject involve determining the amount of Repro-PC-1.0 polynucleotide or polypeptide in a subject sample and comparing that amount to a prognostic amount. A determined amount at a particular prognostic amount provides a prognosis for the subject.

In another aspect, this invention provides a method of detecting a chromosomal translocation of a Repro-PC-1.0 gene comprising the steps of hybridizing a labeled probe of the invention to a chromosome spread from a cell sample to determine the pattern of hybridization and determining whether the pattern of hybridization differs from a normal pattern.

In another aspect, this invention provides methods for the prophylactic or therapeutic treatment of prostate cancer in a subject. One method involves providing prostate cancer cells with an inhibitory polynucleotide of the invention. Another method involves administering to the subject a composition comprising antibodies that specifically bind to Repro-PC-1.0 coupled to a toxin that kills or inhibits the growth of prostate cancer cells. Another method involves altering the hormonal environment of the cancer cells to suppress expression of Repro-PC-1.0.

In another aspect, this invention provides pharmaceutical compositions comprising a pharmaceutically acceptable carrier and pharmacologically effective amount of an inhibitory polynucleotide of the invention or a toxin-conjugated antibody of the invention.

In another aspect, this invention provides polynucleotide and polypeptide vaccines for eliciting a humoral or cell-mediated immune response against Repro-PC-1.0 or cells expressing it. A polypeptide or polynucleotide vaccine for eliciting an immune response against Repro-PC-1.0 comprises an immunogenic Repro-PC-1.0 polypeptide analog or a polynucleotide encoding the analog. In one embodiment, the immunogenic analog bears an MHC Class I or MHC Class II binding motif.

In another aspect, this invention provides a method for eliciting in a subject an immune response against a cell bearing Repro-PC-1.0 on its surface comprising administering to the subject a vaccine of the invention. One method for eliciting an MHC Class Independent cell-mediated immune response involves providing the subject with cells transfected with an expression vector that encodes Repro-PC-1.0 polypeptide, or Repro-PC-1.0 analogs comprising amino acid motifs recognized by MHC Class I molecules.

In another aspect, this invention provides screening methods for determining whether a compound modulates (inhibits or promotes) the expression of Repro-PC-1.0 in a cell. The methods involve contacting the cell with the compound and determining whether the production of Repro-PC-1.0 mRNA or polypeptide are altered (increased, decreased or unchanged) in a statistically significant manner ($p<0.05$).

In another aspect, this invention provides screening methods for determining whether a compound inhibits the activity of Repro-PC-1.0. The methods involve contacting a cell expressing Repro-PC-1.0 with the compound and determining whether exocytotic events have been altered. According to one method, a determination is made as to whether the amount or character of secretions by the cell into the medium is altered by the compound. In another method, the compound is tested for its ability to alter the capacitance across the cell membrane.

In another aspect this invention provides methods for detecting polymorphic forms of Repro-PC-1.0 comprising comparing the identity of a nucleotide or amino acid at a selected position from the sequence of a test Repro-PC-1.0 gene or polypeptide with identity of the nucleotide or amino acid at the corresponding position of native Repro-PC-1.0 (SEQ ID NO: 1 or 2). A difference in identity indicates that the test polynucleotide is a polymorphic form of Repro-PC-1.0.

In another aspect, this invention provides a transgenic non-human animal, preferably a mammal, whose germ cells comprise a recombinant polynucleotide of this invention.

BRIEF DESCRIPTION OF THE DRAWINGS

FIG. 2A shows RNA from LNCaP cells and hybridized with Repro-PC-1.0-specific probe. FIG. 2B shows rehybridization of the same blot with probes for tubulin and actin. Male=male-grown tumors. Female=female-grown rumors. C=LNCaP cells. P=PC3 cells.

FIG. 3 shows the alignment of overlapping clones which, together, produce the Repro-PC-1.0 cDNA of SEQ ID NO: 1.

FIG. 5 shows the alignment of the amino acid sequences of Repro-PC-1.0 (SEQ ID NO:2) and rat synaptotagmin 4 ("SYT4") (SEQ ID NO:5).

FIG. 6 shows the alignment of the internal repeats of PKC-C2 (SEQ ID NO:6), Repro-PC-1.0 "B" repeat (SEQ ID NO:7), synaptotagmin "B" repeat (SEQ ID NO:8, synaptotagmin "A" repeat (SEQ ID NO:9) and Repro-PC-1.0 "A" repeat (SEQ ID NO:10).

DETAILED DESCRIPTION

I. Definitions

Figure 1A:
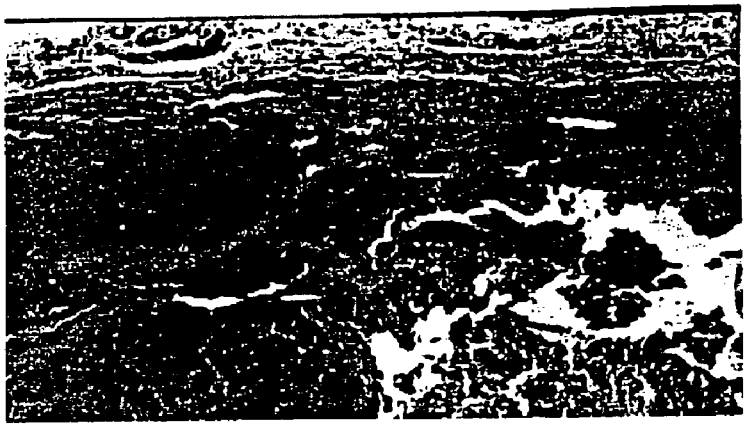
FIGS. 1A–1B are photographs of LNCaP cells grown in male (1A) and female (1B) mice.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, preferred methods and materials are described. As used herein, the following terms have the meanings ascribed to them unless specified otherwise.

"Polynucleotide" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A. U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition or nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

Conventional notation is used herein to portray polypeptide sequences: the left-hand end of a polypeptide sequence is the amino-terminus; the right-hand end of a polypeptide sequence is the carboxyl-terminus.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

A "reference sequence" is a defined sequence used as a basis for a sequence comparison and may be a subset of a larger sequence, e.g., a complete cDNA, protein, or gene sequence.

Because two polynucleotides or polypeptides each may comprise (1) a sequence (i.e., only a portion of the complete polynucleotide or polypeptide sequence) that is similar between the two polynucleotides, or (2) a sequence that is divergent between the two polynucleotides, sequence comparisons between two (or more) polynucleotides or polypeptides are typically performed by comparing sequences of the two polynucleotides over a "comparison window" to identify and compare local regions of sequence similarity.

A "comparison window" refers to a conceptual segment of typically at least 12 consecutive nucleotide or 4 consecutive amino acid residues that is compared to a reference sequence. The comparison window frequently has a length of at least 15 or at least 25 nucleotides or at least 5 or at least 8 amino acids. The comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, Wis.) or by inspection, and the best alignment (i.e., resulting in the highest percentage of homology over the comparison window) generated by any of the various methods is selected.

A subject nucleotide sequence or amino acid sequence is "identical" to a reference sequence if the two sequences are the same when aligned for maximum correspondence over the length of the nucleotide or amino acid sequence.

The "percentage of sequence identity" between two sequences is calculated by comparing two optimally aligned sequences over a comparison window, determining the number of positions at which the identical nucleotide or amino acid occurs in both sequences to yield the number of matched positions, dividing the number of matched positions by the total number of positions in the window of comparison (i.e., the window size), and multiplying the result by 100 to yield the percentage of sequence identity. Unless otherwise specified, the comparison window used to compare two sequences is the length of the shorter sequence.

Alternatively, when percentage of sequence identity is used in reference to polypeptides it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers & Miller, *Computer Applic. Biol. Sci.,* 4: 11–17 (1988); Smith & Waterman, *Adv. Appl. Math.* 2: 482 (1981); Needleman & Wunsch, *J. Mol. Biol.* 48: 443 (1970); Pearson & Lipman, *Proc. Natl. Acad. Sci. USA* 85: 2444 (1988); Higgins & Sharp *Gene,* 73: 237–244 (1988); Higgins & Sharp, *CABIOS* 5: 151–153 (1989); Corpet et al., *Nucleic Acids Research* 16: 10881–90 (1988); Huang et al., *Computer Applications in the Biosciences* 8: 155–65 (1992); and Pearson et al., *Methods in Molecular Biology* 24: 307–31 (1994). Alignment is also often performed by inspection and manual alignment.

A subject nucleotide sequence or amino acid sequence is "substantially identical" to a reference sequence if the subject amino acid sequence or nucleotide sequence has at least 90% sequence identity over a comparison window. Thus, sequences that have at least 95% sequence identity, at least 98% sequence identity or at least 99% sequence identity with the reference sequence are also "substantially identical." Two sequences that are identical to each other are, of course, also "substantially identical".

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T):
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterized fragments produced by digestion with various peptidases. This includes, e.g., Fab' and F(ab)', fragments. The term "antibody," as used herein, also includes antibody fragments either produced by the modification of whole antibodies or those synthesized de novo using recombinant DNA methodologies.

"Immunoassay" refers to an assay that utilizes an antibody to specifically bind an analyte. The immunoassay is characterized by the use of specific binding properties of a particular antibody to isolate, target, and/or quantify the analyte.

"Vaccine" refers to an agent or composition containing an agent effective to confer a therapeutic degree of immunity on an organism while causing only very low levels of morbidity or mortality. Methods of making vaccines are, of course, useful in the study of the immune system and in preventing and treating animal or human disease.

An "immunogenic amount" is an amount effective to elicit an immune response in a subject.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays", Elsevier, New York. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of. e.g., more than 100 nucleotides, is 1×SSC at 45° C. for 15 minutes. An example low stringency wash for a duplex of. e.g., more than 100 nucleotides, is 4–6×SSC at 40° C. for 15 minutes. In general, a signal to noise ratio of 2×(or higher) than that observed for an unrelated probe in the particular hybridization assay indicates detection of a specific hybridization.

An antibody "specifically binds to" or "is specifically immunoreactive with" a protein when the antibody functions in a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

A first sequence is an "antisense sequence" with respect to a second sequence if a polynucleotide whose sequence is the first sequence specifically hybridizes with a polynucleotide whose sequence is the second sequence.

"Substantially pure" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Detecting" refers to determining the presence, absence, or amount of an analyte in a sample, and can include quantifying the amount of the analyte in a sample or per cell in a sample.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds. e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., PD. Fahrlander and A. Klausner, *Bio/Technology* (1988) 6:1165.) Quantitation of the signal is achieved by, e.g., scintillation counting, densitometry, or flow cytometry.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Amplification" refers to any means by which a polynucleotide sequence is copied and thus expanded into a larger number of polynucleotide molecules, e.g., by reverse transcription, polymerase chain reaction, and ligase chain reaction.

"Prognostic value" refers to an amount of an analyte in a subject sample that is consistent with a particular prognosis for a designated disease. The amount (including a zero amount) of the analyte detected in a sample is compared to the prognostic value for the sample such that the relative comparison of the values indicates the likely outcome of the progression of the disease.

"Diagnostic value" refers to a value that is determined for an analyte in a subject sample, which is then compared to a normal range of the analyte in a sample (e.g., from a healthy individual) such that the relative comparison of the values provides a reference value for diagnosing a designated disease. Depending upon the method of detection, the diagnostic value may be a determination of the amount of the analyte, but it is not necessarily an amount. The diagnostic value may also be a relative value, such as a plus or a minus score, and also includes a value indicating the presence or absence of the analyte in a sample.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, or intravenous intraperitoneal injection; or topical, transdermal, or transmucosal administration).

A "subject" of diagnosis or treatment is an animal, such as a mammal, including a human. Non-human animals subject to treatment include, for example, fish, birds, and mammals such as primates, cows, sheep, pigs, horses, dogs and cats.

A "prophylactic" treatment is a treatment administered to a subject who does not exhibit signs of a disease or exhibits only early signs for the purpose of decreasing the risk of developing pathology.

A "therapeutic" treatment is a treatment administered to a subject who exhibits signs of pathology for the purpose of diminishing or eliminating those signs.

II. cDNA Encoding Repro-PC-1.0

A cDNA molecule encoding a prostate cancer-specific marker, called Repro-PC-1.0, has been isolated. The nucleotide sequence and deduced amino acid sequence of the nucleic acid molecule are presented in SEQ ID NO: 1 and SEQ ID NO:2, respectively. This 3891-base nucleotide sequence contains an open reading frame of 1275 bases encoding Repro-PC-1.0 from nucleotide 151 to nucleotide 1425. The deduced amino acid sequence of Repro-PC-1.0 has 425 amino acids.

Analysis of the deduced amino acid sequence or Repro-PC-1.0 shows 90% identity with rat synaptotagmin IV. Amino acid residues 15–37 have sufficient length and hydrophobicity to constitute a transmembrane domain that displays the unusual transmembrane boundaries of other synaptotagmins. Repro-PC1.0 also has two copies of a 116 amino acid direct repeat (amino acids 150–252 and 276–396) that have 34% identity with each other. These repeats are homologous to the C2 regulatory domain of calcium-dependent isoforms of protein kinase C (PKC) and other isoforms of the synaptotagmins.

The synaptotagmins are synaptic vesicle proteins proposed to play a role in regulating synaptic vesicle translocation to the presynaptic release site of the plasma membrane (docking) and/or fusion of these two membranes. Therefore, while not wishing to be limited by theory, it is believed that Repro-PC-1.0 functions in exocytosis and endocytosis pathways.

II. Repro-PC-1.0 Nucleic Acids

Accordingly, this invention provides recombinant polynucleotides comprising nucleotide sequences encoding Repro-PC-b 1.0 proteins, Repro-PC-1.0 analogs or fragments of them, as described herein. Analogs include "active analogs" having the biological activity of Repro-PC-1.0, "inactive analogs" useful, e.g., as decoys, and "immunogenic analogs," which, when presented as an immunogen, elicit the production of an antibody which specifically binds to Repro-PC-1.0. The polynucleotides are useful for expressing the mRNA or polypeptides they encode and in the preparation of probes or primers, among other things.

In one embodiment, the recombinant polynucleotide molecule comprises a nucleotide sequence encoding a sequence of at least 5 amino acids selected from the amino acid sequence of Repro-PC-1.0 (SEQ ID NO:2). The nucleotide sequence can encode a sequence of at least 25 amino acids, at least 100 amino acids or at least 200 amino acids from SEQ ID NO:2. In one embodiment, the nucleotide sequence encodes full-length native Repro-PC-1.0 polypeptide.

The nucleotide sequence can be identical to a sequence from Repro-PC-1.0 cDNA or its complement, or can include degenerate codons. In one embodiment of a nucleotide sequence encoding full-length Repro-PC1.0, the sequence is identical to the coding sequence of Repro-PC1.0 of SEQ ID NO:1. In another embodiment, the nucleotide sequence encodes a Repro-PC-1.0 analog whose amino acid sequence is substantially identical to the amino acid sequence of Repro-PC-1.0 polypeptide (SEQ ID NO:2).

In another embodiment, the polynucleotide encodes a fusion protein between Repro-PC-1.0 polypeptide or Repro-PC-1.0 analog amino acid sequences and a second amino acid sequence.

The polynucleotides of the present invention are cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA from prostate cancer cells using primers based on the DNA sequence of Repro-PC-1.0 of SEQ ID NO: 1. One pair of primers useful for amplifying Repro-PC-1.0 DNA, including allelic variants, is:

5' oligo (109)
Upper Primer, 21-mer, position 109:
5'CAG TTT TCC CTT CAG CAC CTC 3' (SEQ ID NO:3)
3' oligo (3489):
Lower Primer, 30-mer, position 3489:
5' TTC CTT TGT TGT TTC TTT TCT CTT TTC TGA 3' (SEQ ID NO:4)

A wide variety of cloning and in vitro amplification methodologies are well-known to persons of skill. PCR methods are described in, for example, U.S. Pat. No. 4,683,195, Mullis et al. (1987) *Cold Spring Harbor Symp. Quant. Biol.* 51:263; and Erlich, ed., *PCR Technology*, (Stockton Press, NY, 1989). Polynucleotides also can be isolated by screening genomic or cDNA libraries with probes selected from the sequences of SEQ ID NO: 1 under stringent hybridization conditions.

Mutant versions of the proteins can be made by site-specific mutagenesis of other polynucleotides encoding the proteins, or by random mutagenesis caused by increasing the error rate of PCR of the original polynucleotide with 0.1 mM MnCl$_2$ and unbalanced nucleotide concentrations.

This invention also provides expression vectors. e.g., recombinant polynucleotide molecules comprising expression control sequences operatively linked to a nucleotide sequence encoding the target polypeptide. Expression vectors can be adapted for function in prokaryotes or eukaryotes by inclusion of appropriate promoters, replication sequences, markers, etc. for transcription and translation of mRNA. The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor. NY, (1989) and *Current Protocols in Molecular Biology*, F. M. Ausubel et al., eds., (Current Protocols, a joint venture between Greene Publishing Associates, Inc. and John Wiley & Sons. Inc.) Useful promoters for such purposes include a metallothionein promoter, a constitutive adenovirus major late promoter, a dexamethasone-inducible MMTV promoter, a SV40 promoter, a MRP pollII promoter, a constitutive MPSV promoter, a tetracycline-inducible CMV promoter (such as the human immediate-early CMV promoter), and a constitutive CMV promoter. A plasmid useful for gene therapy can comprise other functional elements, such as selectable markers, identification regions, and other genes. Recombinant DNA expression plasmids can also be used to prepare the polynucleotides of the invention for delivery by means other than by gene therapy, although it may be more economical to make short oligonucleotides by in vitro chemical synthesis.

Methods for transfecting genes into mammalian cells and obtaining their expression for in vitro use or for gene therapy, are well known to the art. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990).

Expression vectors useful in this invention depend on their intended use. Such expression vectors must, of course, contain expression and replication signals compatible with the host cell. Expression vectors useful for expressing the protein of this invention include viral vectors such as alpha viruses, retroviruses, adenoviruses and adeno-associated viruses, plasmid vectors, cosmids, liposomes and the like. Viral and plasmid vectors are preferred for transfecting mammalian cells. The expression vector pcDNA1 (Invitrogen, San Diego, Calif.), in which the expression control sequence comprises the CMV promoter, provides good rates of transfection and expression. Adeno-associated viral vectors are useful in the gene therapy methods of this invention.

The construct can also contain a tag to simplify isolation of the protein. For example, a polyhistidine tag of. e.g., six histidine residues, can be incorporated at the amino terminal end of the protein. The polyhistidine tag allows convenient isolation of the protein in a single step by nickel-chelate chromatography.

In another embodiment, endogenous genes are transcribed by operatively linking them to expression control sequences supplied endogenously that recombine with genomic DNA. In one method, one provides the cell with a recombinant polynucleotide containing a targeting sequence, which permits homologous recombination into the genome upstream of the transcriptional start site of target gene; the expression control sequences; an exon of the target gene; and an unpaired splice-donor site which pairs with a splice acceptor in the target gene. Such methods are discussed in Treco et al., WO 94/12650; Treco et al., WO 95/31560 and Treco et al., WO 96/29411.

The invention also provides recombinant cells comprising an expression vector for expression of the nucleotide sequences encoding a polypeptide of this invention. Host cells can be selected for high levels of expression in order to purify the protein. Mammalian cells are preferred for this purpose, but prokaryotic cells, such as *E. coli*, also are useful. The cell can be, e.g., a recombinant cell in culture or a cell in vivo.

IV. Polynucleotide Probes and Primers

This invention provides polynucleotide probes and primers that specifically hybridize to a subsequence of Repro-PC-1.0 cDNA or its complement under stringent hybridization conditions. The probes and primers of this invention are polynucleotides of at least 7 nucleotides, at least 10 nucleotides, at least 15 nucleotides, at least 20 nucleotides or at least 25 nucleotides. In one embodiment, the sequence of the polynucleotide is a contiguous sequence from SEQ ID NO: 1 or its complement. Any suitable region of the Repro-PC-1.0 gene may be chosen as a target for polynucleotide hybridization. Nucleotide substitutions, deletions, and additions may be incorporated into the polynucleotides as long as the characteristic ability to specifically hybridize to the target sequence or its complement is retained. Nucleotide sequence variation may result from sequence polymorphisms of various alleles, minor sequencing errors, and the like.

The probes and primers of the invention are useful as probes in hybridization assays, such as Southern and Northern blots, for identifying polynucleotides having a nucleotide sequence encoding a Repro-PC-1.0 polypeptide, and as primers for amplification procedures. The probes and primers of the invention are also useful in detecting the presence, absence or amount of Repro-PC-1.0 in tissue biopsies and histological sections where the detection method is carried out in situ, typically after amplification of Repro-PC-1.0 sequences using a primer set.

The probes and primers of this invention also are useful for identifying allelic forms of Repro-PC-1.0 and animal cognate genes. Probes and primers can be used to screen human or animal genomic DNA or cDNA libraries under, e.g., stringent conditions. DNA molecules that specifically hybridize to the probe are then further examined to determine whether they are Repro-PC-1.0 allelic variants or animal cognates.

The probes also are useful in oligonucleotide arrays. Such arrays are used in hybridization assays to check the identity of bases in a target polynucleotide. In essence, when a target hybridizes perfectly to a probe on the array, the target contains the nucleotide sequence of the probe. When the target hybridizes less well, or does not hybridize at all, then the target and probe differ in sequence by one or more nucleotide. By proper selection of probes, one can check bases on a target molecule. See, e.g., Chee et al., WO 95/11995. The use the Repro-PC-1.0 sequence in genomics is described further below.

In one embodiment, the polynucleotide further comprises a label. A detectable moiety bound to either an oligonucleotide primer or a probe is subsequently used to detect hybridization of an oligonucleotide primer to the RNA component. Detection of labeled material bound to a Repro-PC-1.0 polynucleotide in a sample provides a means of determining a diagnostic or prognostic value.

Although primers and probes can differ in sequence and length, the primary differentiating factor is one of function: primers serve as an initiation point for DNA synthesis of a target polynucleotide, as in RT and PCR reactions, while probes are typically used for hybridization to and detection of a target polynucleotide. Typical lengths of primers or probes can range from 7–50 nucleotides, preferably from 10–40 nucleotides, and most preferably from 15–35 nucleotides. A primer or probe can also be labeled with a detectable moiety for detection of hybridization of the primer or probe to the target polynucleotide.

In general, those of skill in the an recognize that the polynucleotides used in the invention include both DNA and RNA molecules and naturally occurring modifications thereof, as well as synthetic, non-naturally occurring analogs of the same, and heteropolymers, of deoxyribonucleotides, ribonucleotides, and/or analogues of either. The particular composition of a polynucleotide or polynucleotide analog will depend upon the purpose for which the material will be used and the environment in which the material will be placed. Modified or synthetic, non-naturally occurring nucleotides have been designed to serve a variety of purposes and to remain stable in a variety of environments, such as those in which nucleases are present.

Oligonucleotides preferably are synthesized, e.g., on an Applied BioSystems or other commercially available oligonucleotide synthesizer according to specifications provided by the manufacturer. Oligonucleotides may be prepared using any suitable method, such as the phosphotriester and phosphodiester methods, or automated embodiments thereof. In one such automated embodiment, diethylphosphoramidates are used as starting materials and may be synthesized as described by Beaucage er al., *Tetrahedron Letters* 22: 1859 (1981), and U.S. Pat. No. 4,459,066.

Polynucleotides, e.g., probes, also can be recombinantly produced through the use of plasmids or other vectors.

V. Methods for Detecting Repro-PC-1.0 Polynucleotides

The probes and primers of this invention are useful, among other things, in detecting Repro-PC-1.0 polynucleotides in a sample. A method for detecting the presence, absence or amount of a Repro-PC-1.0 polynucleotide in a sample involves two steps: (1) specifically hybridizing a polynucleotide probe or primer to a Repro-PC-1.0 polynucleotide, and (2) detecting the specific hybridization.

For the first step of the method, the polynucleotide used for specific hybridization is chosen to hybridize to any suitable region of Repro-PC-1.0. The polynucleotide can be a DNA or RNA molecule, as well as a synthetic, non-naturally occurring analog of the same. The polynucleotides in this step are polynucleotide primers and polynucleotide probes disclosed herein.

For the second step of the reaction, any suitable method for detecting specific hybridization of a polynucleotide to Repro-PC-1.0 may be used. Such methods include, e.g., amplification by extension of a hybridized primer using reverse transcriptase (RT); extension of a hybridized primer using RT-PCR or other methods of amplification; and in situ detection of a hybridized primer. In in situ hybridization, a sample of tissue or cells is fixed onto a glass slide and permeablized sufficiently for use with in situ hybridization techniques. Detectable moieties used in these methods include, e.g., labeled polynucleotide probes; direct incorporation of label in amplification or RT reactions, and labeled polynucleotide primers.

Often, cell extracts or tissue samples used in methods for determining the amount of a polynucleotide in a sample will contain variable amounts of cells or extraneous extracellular matrix materials. Thus, a method for determining the cell number in a sample is important for determining the relative amount per cell of a test polynucleotide such as Repro-PC-1.0. A control for cell number and amplification efficiency is useful for determining diagnostic values for a sample of a potential cancer, and a control is particularly useful for comparing the amount of test polynucleotide such as Repro-PC-1.0 in sample to a prognostic value for prostate cancer. A preferred embodiment of the control RNA is endogenously expressed 28S rRNA. (See, e.g., Khan et al., *Neurosci. Lett.* 147: 114–117 (1992) which used 28S rRNA as a control, by diluting reverse transcribed 28S rRNA and adding it to the amplification reaction.)

VI. Inhibitory Polynucleotides for Inhibiting Repro-PC-1.0 Expression

A. General

This invention also provides inhibitory polynucleotides directed against Repro-PC-1.0 polynucleotides that inhibit Repro-PC-1.0 expression and, therefore inhibit its activity in a cell. Inhibitory polynucleotides can inhibit Repro-PC-1.0 activity in a number of ways. According to one mechanism, the polynucleotide prevents transcription of the Repro-PC-1.0 gene (for instance, by triple helix formation). In another mechanism, the polynucleotide destabilizes the Repro-PC-1.0 and reduces its half-life. In another mechanism, the polynucleotide inhibits assembly the RNA component into the Repro-PC-1.0 by binding to Repro-PC-1.0.

An inhibitory polynucleotide is a polynucleotide that is capable of specifically hybridizing with a target polynucleotide and that interferes with the transcription, processing, translation or other activity the target polynucleotide. Inhibitory polynucleotides generally are single-stranded and have a sequence of at least 7, 8, 9, 10, or 11 nucleotides capable of specifically hybridizing to the target sequence. RNA sequences generally require a sequence of at least 10 nucleotides for specific hybridization. Inhibitory polynucleotides include, without limitation, antisense molecules, ribozymes, sense molecules and triplex-forming molecules. In one embodiment, the inhibitory polynucleotide is no more than about 50 nucleotides long.

While not wishing to be limited by theory, it is believed that inhibitory polynucleotides inhibit the function of a target, in part, by binding to the appropriate target sequence. An inhibitory polynucleotide can inhibit DNA replication or DNA transcription by, for example, interfering with the attachment of DNA or RNA polymerase to the promoter by binding to a transcriptional initiation site or a template. It can interfere with processing of mRNA, poly(A) addition to mRNA or translation of mRNA by, for example, binding to regions of the RNA transcript such as the ribosome binding site. It can promote inhibitory mechanisms of the cells, such as promoting RNA degradation via RNase action. The inhibitory polynucleotide can bind to the major groove of the duplex DNA to form a triple helical or "triplex" structure. Methods of inhibition using inhibitory polynucleotides therefore encompass a number of different approaches to altering expression of specific genes that operate by different mechanisms. These different types of inhibitory polynucleotide technology are described in C. Helene and J. Toulme, (1990) *Biochim. Biophys. Acta.,* 1049:99–125.

Antisense polynucleotides can include deoxyribonucleotides or ribonucleotides. They can be chemically modified so as to improve stability in the body. Properties of the polynucleotide can be engineered to impart stability (e.g., nuclease resistance), tighter binding or the desired $T_m$. See, e.g., International patent publication No. 94/12633.

The general approach to constructing various polynucleotides useful in inhibitory polynucleotide therapy has been reviewed by A. R. Vander Krol et al. (1988), *Biotechniques* 6:958–976, and by C. A. Stein et al., (~1988) *Cancer Res.* (1988) 48:2659–2668. See also *Oligodeoxynucleotides: Antisense Inhibitors of Gene Expression*, Cohen. J. S., editor, MacMillan Press. London, pages 79–196 (1989), and *Antisense RNA and DNA*, (1988), D. A. Melton. Ed., Cold Spring Harbor Laboratory, Cold Spring Harbor, N.Y. In certain embodiments inhibitory polynucleotides comprise a derivatized substituent which is substantially non-interfering with respect to hybridization of the inhibitory polynucleotide to the target polynucleotide.

B. Antisense

This invention provides antisense polynucleotides capable of specifically to hybridizing to a target sequence of Repro-PC-1.0. Antisense polynucleotides are useful in vitro or in vivo to inhibit the activity of Repro-PC-1.0.

The antisense polynucleotides of this invention comprise an antisense sequence of at least 7 nucleotides that specifically hybridize to a sequence from Repro-PC-1.0 and, more particularly, mammalian Repro-PC-1.0 and human Repro-PC-1.0. The antisense sequence can be between about 10 and about 50 nucleotides or between about 15 and about 35 nucleotides. In other embodiments, antisense polynucleotides are polynucleotides of less than about 100 nucleotides or less than about 200 nucleotides. Accordingly, a sequence of the antisense polynucleotide can specifically hybridize to all or part of the Repro-PC-1.0, such as antisense polynucleotides to the Repro-PC-1.0 gene or its transcribed RNA. In one embodiment, the sequence of the polynucleotide contains within it the antisense sequence. In this case, the antisense sequence is contained within a polynucleotide of longer sequence. In another embodiment, the sequence of the polynucleotide consists essentially of, or is, the antisense sequence. Thus, for example, the antisense polynucleotide can be a polynucleotide of less than about 50 nucleotides in a sequence that specifically hybridizes to the target sequence.

Generally, to assure specific hybridization, the antisense sequence is substantially complementary to the target sequence in Repro-PC-1.0. In certain embodiments, the antisense sequence is exactly complementary to the target sequence. The antisense polynucleotides may include nucleotide substitutions, additions, deletions, or transpositions, so long as specific binding to the relevant target sequence corresponding to Repro-PC-1.0 mRNA or its gene is retained as a functional property of the polynucleotide.

The antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, polyamide nucleic acid, phosphorothioate, etc.), among others.

For general methods relating to antisense polynucleotides, see *Antisense RNA and DNA*, (1988), D. A. Melton, Ed., Cold Spring Harbor Laboratory, Cold Spring Harbor, N.Y.). For a review of antisense therapy, see, e.g., Uhlmann et al., *Chem. Reviews,* 90:543–584 (1990).

C. Ribozymes

Cleavage of Repro-PC-1.0 can be induced by the use of ribozymes or catalytic RNA. In this approach, the ribozyme would contain either naturally occurring RNA (ribozymes) or synthetic nucleic acids with catalytic activity. Bratty et al., (1992) *Biochim. Biophys. Acta.,* 1216:345–59 (1993) and Denhardt, (1992) *Ann. N.Y. Acad. Sci.,* 660:70–76 describe methods for making ribozymes.

Unlike the antisense and other polynucleotides described above, which bind to an RNA or a DNA, a ribozyme not only binds but also specifically cleaves and thereby potentially inactivates a target RNA. Such a ribozyme can comprise 5'- and 3'-terminal sequences complementary to the Repro-PC-1.0 RNA.

Optimum target sites for ribozyme-mediated inhibition of activity can be determined as described by Sullivan et al., PCT patent publication No. 94/02595 and Draper et al., PCT patent publication No. 93/23569. As described by Hu et al., PCT patent publication No. 94/03596, antisense and ribozyme functions can be combined in a single polynucleotide. Upon review of the RNA sequence of Repro-PC-1.0 those in the art will note that several useful ribozyme target sites are present and susceptible to cleavage by, for example, a hammerhead motif ribozyme.

Such engineered ribozymes can be expressed in cells or can be transferred by a variety of means (e.g., liposomes, immunoliposomes, biolistics, direct uptake into cells, etc.). Other forms of ribozymes (group 1 intron ribozymes (Cech (1995) *Biotechnology* 13: 323); hammerhead ribozymes (Edgington (1992) *Biotechnology* 10: 256) can be engineered on the basis of the disclosed Repro-PC-1.0 sequence information to catalyze cleavage of Repro-PC-1.0 RNA. Moreover, ribozymes can comprise one or more modified nucleotides or modified linkages between nucleotides, as described above.

D. Other Inhibitory Polynucleotides

In addition to the antisense and ribozyme inhibitory polynucleotides, one can construct polynucleotides that will bind to duplex nucleic acid either in the folded RNA component or in the gene for the RNA component, forming a triple helix-containing or triplex nucleic acid to inhibit Repro-PC-1.0 activity. Such polynucleotides of the invention are constructed using the base-pairing rules of triple helix formation and the nucleotide sequence of the RNA component (Cheng et al. (1988) *J. Biol. Chem.* 263: 15110; Ferrin and Carnerini-Otero (1991) *Science* 354: 1494; Ramdas et al. (1989) *J. Biol. Chem.* 264: 17395; Strobel et al. (1991) *Science* 254: 1639; Hsieh et al. (1990) op.cit.; Rigas et al. (1986) *Proc. Natl. Acad. Sci.* (*U.S.A.*) 83: 9591. Such polynucleotides can block Repro-PC-1.0 activity in a number of ways, including by preventing transcription of the Repro-PC-1.0 gene.

Typically, and depending on mode of action, the triplex-forming polynucleotides of the invention comprise a sequence large enough to form a stable triple helix but small enough, depending on the mode of delivery, to administer in vivo.

E. Methods for Making Inhibitory Polynucleotides

Inhibitory polynucleotides can be made chemically or recombinantly.

1. Chemical Synthesis

Small inhibitory polynucleotides for direct delivery can be made by chemical synthesis. Chemically synthesized polynucleotides can be DNA or RNA, or can include nucleotide analogs or backbones that are not limited to phosphodiester linkages.

2. Recombinant Production

For delivery into cells or for gene therapy methods, recombinant production of inhibitory polynucleotides through the use of expression vectors is particularly useful. Accordingly, this invention also provides expression vectors, e.g., recombinant polynucleotide molecules comprising expression control sequences operatively linked to the nucleotide sequence encoding the inhibitory polynucleotide.

VII. Repro-PC-1.0 Polypeptides

This invention also provides purified, recombinant Repro-PC-1.0 polypeptide and Repro-PC-1.0 analogs. Recombinant Repro-PC-1.0 polypeptide includes the polypeptide whose amino acid sequence is presented in SEQ ID NO:2, as well as allelic variants of it. Repro-PC-1.0 analogs include active Repro-PC-1.0 analogs, inactive Repro-PC-1.0 analogs and immunogenic Repro-PC-1.0 analogs.

Repro-PC-1.0 polypeptide refers to native Repro-PC-1.0, the polypeptide whose amino acid sequence is the amino acid sequence of SEQ ID NO:2, and to allelic variants of it. Polynucleotide molecules that encode allelic variants of Repro-PC-1.0 are isolatable from prostate cancer cell cDNA or genomic DNA and typically hybridize under stringent conditions to the nucleotide sequence encoding Repro-PC-1.0 (SEQ ID NO: 1). They can be obtained by amplification using. e.g., PCR primers taken from the sequence of Repro-PC-1.0 described herein.

Repro-PC-1.0 polypeptides are useful as immunogens to elicit the production of anti-Repro-PC-1.0 antibodies, as affinity capture molecules to isolate such antibodies from a mixture, and as controls in diagnostic methods aimed at detecting Repro-PC-1.0 in a sample.

A Repro-PC-1.0 analog is a polypeptide whose sequence is not naturally occurring but is substantially identical over its sequence to a sequence of native Repro-PC-1.0. Repro-PC-1.0 analogs include active Repro-PC-1.0 analogs, inactive Repro-PC-1.0 analogs and immunogenic Repro-PC-1.0 analogs. Repro-PC-1.0 analogs include fusion proteins, i.e., polypeptides having a Repro-PC-1.0/Repro-PC-1.0 analog moiety fused with another polypeptide moiety at its amino- or carboxy-terminal end.

Active Repro-PC-1.0 analogs have the biological activity of Repro-PC-1.0. Repro-PC-1.0 is believed to function in exocytosis and endocytosis pathways. Generally, active Repro-PC-1.0 analogs have at least 95% sequence identity with native Repro-PC-1.0. Active Repro-PC-1.0 analogs can be produced by, for example, introducing conservative amino acid substitutions into the sequence of native Repro-PC-1.0. Changes in the amino acid sequence outside the direct repeat sequences or outside amino acids 40–140 are most likely to be tolerated. Amino acids around 1–15, 268–275 and 397–425 probably are highly mutable. Amino acids in the transmembrane region. e.g., amino acids 15–37 (SEQ ID NO:2) should not be substituted with hydrophilic amino acids. Active fragments of Repro-PC-1.0 can be identified empirically by truncating the protein from either the amino-terminus or the carboxy-terminus to generate fragments, and testing the resulting fragments for Repro-PC-1.0 activity. More specifically, the following substitutions in Repro-PC-1.0 are expected to yield analogs that have Repro-PC-1.0 activity: N79S (i.e., substitute N at position 79 with S); V87L; S133A; E268D and V421M.) These substitutions occur in areas that are not part of the following major motifs sharing identity with rat synaptotagmin IV: PKA phosphorylation site, CK2 phosphorylation site. PKC phosphorylation site, N-myristoylation site, PKC C2 domain and the transmembrane domain.

Inactive Repro-PC-1.0 analogs are polypeptides of at least 5 amino acids whose amino acid sequence over its length is substantially identical to native Repro-PC-1.0. Inactive Repro-PC-1.0 analogs include, for example, polypeptides encoding fragments of Repro-PC-1.0. Useful fragments of Repro-PC-1.0 include polypeptides comprising the sequence of one or both of the 116 amino acid direct repeats of Repro PC-1.0. Another useful fragment of Repro-PC-1.0 is one that lacks the transmembrane region and, therefore, does not anchor into the cell membrane. These inactive analogs are useful as inhibitory polypeptide mimics or decoys. When expressed in a cell they compete with Repro-PC-1.0 polypeptides for interaction with molecules that naturally interact with Repro-PC-1.0. Fragments generally are at least 10, 50 or 100 amino acids long.

Immunogenic Repro-PC-1.0 analogs are polypeptides having a sequence of at least 5 amino acids selected from native Repro-PC-1.0 and which, when presented to an animal as an immunogen, elicit a humoral or cell-mediated immune response. This includes polypeptides comprising an amino acid sequence which is an epitope from Repro-PC-1.0, such as immunogenic fragments of Repro-PC-1.0. Repro-PC-1.0 protein analogs optionally are in isolated form.

Repro-PC-1.0 and analogs are most easily produced recombinantly, as described herein. Recombinant Repro-PC-1.0 can be purified by affinity purification. In one method, recombinant Repro-PC-1.0 analogs comprise a polyhistidine tag. The protein is purified on a nickel-chelate affinity matrix. In another method. Repro-PC-1.0 is purified using an affinity matrix carrying anti-Repro-PC-1.0 antibodies.

VIII. Antibodies and Hybridomas

In one aspect this invention provides a composition comprising an antibody that specifically binds Repro-PC-1.0 polypeptides. Antibodies preferably have affinity of at least $10^6$ $M^{-1}$, $10^7$ $M^{-1}$, $10^8$ $M^{-1}$, or $10^9$ $M^{-1}$. This invention contemplates both polyclonal and monoclonal antibody compositions.

In one embodiment this invention provides immunotoxins against Repro-PC-1.0-expressing cells. Immunotoxins are antibodies and the like as described herein coupled to a compound, e.g., a toxin, that is toxic to a target cell. Toxins can include, for example, radioactive isotopes, ricin, cisplatin, antisense molecules, Diphteria toxin, *Pseudomonas* exotoxin A or *Bacillus anthracis* protective antigen. Immunotoxins bind to cancer cells that express Repro-PC-1.0 and kill them. They are useful in the therapeutic methods of this invention. The antibodies of the invention have many uses. For example, such antibodies are useful for detecting Repro-PC-1.0 polypeptides in immunoassays. The antibodies also can be used to screen expression libraries for particular expression products such as mammalian Repro-PC-1.0. These are useful for detecting or diagnosing various pathological conditions related to the presence of the respective antigens. Usually the antibodies in such a procedure are labeled with a moiety allowing easy detection of presence of antigen by antibody binding. Antibodies raised against Repro-PC-1.0 can also be used to raise anti-idiotypic antibodies.

A. Production of Antibodies

A number of immunogens are used to produce antibodies that specifically bind Repro-PC-1.0 polypeptides. Full-length Repro-PC-1.0 is a suitable immunogen. Typically, the immunogen of interest is a peptide of at least about 3 amino acids, more typically the peptide is 5 amino acids in length, preferably, the fragment is 10 amino acids in length and more preferably the fragment is 15 amino acids in length or greater. The peptides can be coupled to a carrier protein (e.g., as a fusion protein), or are recombinantly expressed in an immunization vector. Antigenic determinants on peptides to which antibodies bind are typically 3 to 10 amino acids in length. Naturally occurring polypeptides are also used either in pure or impure form.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods for producing polyclonal antibodies are known to those of skill in the art. In brief, an immunogen, preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan (1991) *Current Protocols in Immunology* Wiley/Greene, NY; and Harlow and Lane (1989) *Antibodies: A Laboratory Manual* Cold Spring Harbor Press, NY.

Antibodies, including binding fragments and single chain recombinant versions thereof, against predetermined fragments of Repro-PC-1.0 proteins are raised by immunizing animals. e.g., with conjugates of the fragments with carrier proteins as described above.

Monoclonal antibodies are prepared from cells secreting the desired antibody. These antibodies are screened for binding to normal or modified polypeptides, or screened for agonistic or antagonistic activity, e.g., activity mediated through Repro-PC-1.0. In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.: and Kohler and Milstein (1975) *Nature* 256: 495–497.

Other suitable techniques involve selection of libraries of recombinant antibodies in phage or similar vectors. See, Huse et al. (1989) *Science* 246: 1275–1281: and Ward, et al. (1989) *Nature* 341: 544–546.

Frequently, the polypeptides and antibodies will be labeled by joining, either covalently or non-covalently, a substance which provides for a detectable signal. A wide variety or labels and conjugation techniques are known and are reported extensively in both the scientific and patent literature. Also, recombinant immunoglobulins may be produced. See, Cabilly, U.S. Pat. No. 4,816,567; and Queen et al. (1989) *Proc. Nat'l Acad. Sci. USA* 86: 10029–10033.

The antibodies of this invention are also used for affinity chromatography in isolating Repro-PC-1.0 proteins. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified Repro-PC-1.0 polypeptides are released.

An alternative approach is the generation of humanized immunoglobulins by linking the CDR regions of non-human antibodies to human constant regions by recombinant DNA techniques. See Queen et al., U.S. Pat. No. 5,585,089.

A further approach for isolating DNA sequences which encode a human monoclonal antibody or a binding fragment thereof is by screening a DNA library from human B cells according to the general protocol outlined by Huse et al., *Science* 246:1275–1281 (1989) and then cloning and amplifying the sequences which encode the antibody (or binding fragment) of the desired specificity. The protocol described by Huse is rendered more efficient in combination with phage display technology. See, e.g., Dower et al., WO 91/17271 and McCafferty et al., WO 92/01047. Phage display technology can also be used to mutagenize CDR regions of antibodies previously shown to have affinity for Repro-PC-1.0 protein receptors or their ligands. Antibodies having improved binding affinity are selected.

In another embodiment of the invention, fragments of antibodies against Repro-PC-1.0 protein or protein analogs are provided. Typically, these fragments exhibit specific binding to the Repro-PC-1.0 protein receptor similar to that of a complete immunoglobulin. Antibody fragments include separate heavy chains, light chains Fab, Fab' F(ab')$_2$ and Fv. Fragments are produced by recombinant DNA techniques, or by enzymic or chemical separation of intact immunoglobulins.

IX. Methods for Detecting Repro-PC-1.0 Polypeptides

Repro-PC-1.0 polypeptides can be identified by any methods known in the art. In one embodiment, the methods involve detecting the polypeptide with a ligand that specifically recognizes the polypeptide. The antibodies of the invention are particularly useful for specific detection of Repro-PC-1.0 polypeptides. A variety of antibody-based detection methods are known in the art. These include, for example, radioimmunoassay, sandwich immunoassays (including ELISA), Western blot, isolation on antibodies bound to a solid phase and in situ detection with labeled antibodies. Another method for detecting Repro-PC-1.0 polypeptides involves identifying the polypeptide according to its mass through, for example, gel electrophoresis, mass spectrometry or HPLC. Subject samples can be taken from any number of appropriate sources, such as blood, urine, tissue biopsy (e.g., lymph node tissue), etc.

X. Diagnostic, Monitoring and Prognostic Methods

Repro-PC-1.0 has been found in all prostate adenocarcinoma tissue tested. Also, it is virtually undetectable in cells other than prostate cancer cells. Therefore, Repro-PC-1.0 is both a highly selective and highly specific marker for prostate cancer. Accordingly, the methods described herein for detecting Repro-PC-11.0 polynucleotides or Repro-PC-1.0 polypeptides in a sample are useful in methods for diagnosing prostate cancer, monitoring its progress or treatment, and determining patient prognosis. The methods of the present invention allow cancerous conditions to be detected with increased confidence and at an earlier stage, before cells are detected as cancerous based on pathological characteristics. It is, of course, understood by diagnosticians that diagnostic tests are measured by their degree of specificity and sensitivity. Tests which are not perfectly specific or sensitive are, nevertheless, useful in diagnosis because they provide useful information which, in combination with other evidence, can provide a definitive diagnosis or indicate a course of treatment.

Methods for diagnosis involve determining a diagnostic amount of Repro-PC-1.0 (e.g., mRNA, cDNA or polypeptide) in a patient sample and comparing that amount with a normal range expected to be found in the sample. Repro-PC-1.0 mRNA or polypeptide has not been detected in normal prostate tissue, and the normal range is no higher than background detection. Therefore, any positive diagnostic amount detected above background is a positive sign of prostate cancer. The samples used to determine the normal range of Repro-PC-1.0 can be normal samples from the individual to be tested, or normal samples from other individuals not suffering from the disease condition.

In one embodiment, methods of diagnosing prostate cancer involve detecting Repro-PC-1.0 on the surface of prostate cancer cells. Cells expressing the protein display the amino terminal section of Repro-PC-1.0 on their surfaces. Therefore, antibodies that recognize the amino terminus of Repro-PC-1.0 are particularly useful for this purpose. Such antibodies can be made, for example, by immunizing an animal with a fragment of Repro-PC-1.0 that contains amino acids from 1 to about 15 of SEQ ID NO:2. In this case, the test cells are exposed to a labeled antibody. Specific binding of the antibody to the cell indicates that the cell expresses Repro-PC-1.0 and is a positive indication that the cell is a prostate cancer cell.

Prostate cancer cells can metastasize even before the cancer is detectable through histopathology. The diagnostic tests of this invention allow one to detect metastatic cells in, for example, the lymph nodes or the blood, by detecting Repro-PC-1.0.

A variety of patient samples can be used in the methods of the invention. For example, cell extracts, cultured cells, or tissue samples provide convenient samples for use with the methods of the invention. The methods of the invention can use samples either in solution or extracts, for example, with RT-PCR, or samples such as tissue sections for in situ methods of detection. Samples can also be obtained from sources such as cells collected from bodily fluids and wastes, e.g., urine, sputum, and blood; washes, e.g., bladder and lung; and fine-needle biopsies. e.g., from prostate; cellular materials; whole cells; tissue and cell extracts; RNA extracted from tissue and cells; and histological sections of tissue.

Methods for monitoring the course of prostate cancer involve determining the amount of Repro-PC-1.0 in a sample at a first and second time. The times can be during routine physical examinations or during a course of treatment for prostate cancer. As prostate cancer appears and/or progresses, the amount of Repro-PC-1.0 in a sample is expected to increase. Regression or cure of prostate cancer are accompanied by a decrease or elimination of Repro-PC-1.0 in a sample.

The stage of a rumor is an indication of patient prognosis. It has been found that more differentiated prostate cancer tumors, as determined by Gleason staining, express higher levels of Repro-PC-1.0. Therefore, by comparing a measured amount of Repro-PC-1.0 in a subject sample with amounts of Repro-PC-1.0 associated with various rumor stages, one can provide a prognosis for the subject. Such a prognostic value is useful in planning a course of treatment for the subject.

The diagnostic and prognostic methods can also be carried out in conjunction with other diagnostic or prognostic tests. In some instances, such combination tests can provide useful information regarding the progression of a disease, although the present methods for testing for Repro-PC-1.0 provide much useful information in this regard.

Another diagnostic method of the invention involves the administration to a subject of a labeled composition that specifically binds to cells bearing Repro-PC-1.0, such as labelled antibodies. Then, the localization of the label is determined by any of the known radiologic methods. Any conventional method for visualizing diagnostic imaging can be used. Usually gamma- and positron-emitting radioisotopes are used for camera imaging and paramagnetic isotopes are used for MRI.

The Repro-PC-1.0 gene is located on chromosome 18. A translocation at this site can result in alteration of Repro-PC-1.0 activity, such as activated transcription or changed function. Chromosomal translocations in the vicinity of the Repro-PC-1.0 gene can be detected by hybridizing a labeled probe of this invention to a chromosome spread. A translocation, duplication or deletion can be identified by aberrant hybridization patterns compared to normal. Such tests are useful in detecting genetic abnormalities such as familial disposition to prostate cancer, or early onset of the disease. A method for fluorescent in situ hybridization of chromosomes is provided in the Examples.

The present invention also provides for kits for performing the diagnostic and prognostic method of the invention. Such kits include a polynucleotide probe or primer, or an antibody specific for Repro-PC-1.0 and instructions to use the reagents to detect Repro-PC-1.0 in a patient sample.

XI. Methods for Inhibiting Repro-PC-1.0 Expression or Activity and of Treating Prostate Cancer Inhibiting Repro-PC-1.0 expression or activity changes a prostate cancer cell from metastatic to non-metastatic. Inhibiting Repro-PC-1.0 expression or activity is useful in vivo in the prophylactic and therapeutic treatment of prostate cancer or other conditions involving Repro-PC-1.0 expression. Accordingly, this invention provides methods for inhibiting Repro-PC-1.0 expression or activity. The methods involve contacting a prostate cancer cell, in vitro or in vivo, with an inhibitory polynucleotide, an immunotoxin or another compound that inhibits Repro-PC-1.0 expression or activity.

A. Delivery of Inhibitory Polynucleotides

This invention contemplates a variety of means for delivering an inhibitory polynucleotide to a subject including, for example, direct uptake of the molecule by a cell from solution, facilitated uptake through lipofection (e.g., liposomes or immunoliposomes), particle-mediated transfection, and intracellular expression from an expression cassette having an expression control sequence operably linked to a nucleotide sequence that encodes the inhibitory polynucleotide. Methods useful for delivery of polynucleotides for therapeutic for therapeutic purposes are described in Inouye et al., U.S. Pat. No. 5,272,065.

B. Pharmaceutical Compositions and Treatment

Agents, such as inhibitory polynucleotides, immunotoxins or other compounds that inhibit Repro-PC-1.0 expression or activity preferably are delivered in pharmaceutical compositions comprising the agent and a pharmaceutically acceptable carrier. The agent can be administered by any route that gives it access to cells expressing Repro-PC-1.0, for example, prostate tumor cells. This includes, for example, aqueous solutions for enteral, parenteral or transmucosal administration, e.g., for intravenous administration, as tonics and administration to mucous or other membranes as, for example, nose or eye drops; solid and other non-aqueous compositions for enteral or transdermal delivery, e.g., as pills, tablets, powders or capsules; transdermal or transmucosal delivery systems for topical administration, and aerosols or mists for delivery by inhalation. One advantage of delivery by a mode that is easy to administer, e.g., enteral or by intravenous or intramuscular injection is that such modes mimic possible modes of delivery should the agent be formulated as a pharmaceutical.

In one embodiment, the pharmaceutical composition is in the form of a unit dose which contains a pharmacologically effective amount of the Repro-PC-1.0-inhibitory compound. The unit dose, taken as part of a therapeutic regimen, results in inhibition of growth of prostate cancer cells. Thus, the pharmaceutical compositions of the invention, whatever the form, are administered in a pharmacologically effective amount to the subject.

The amount of the pharmaceutical composition delivered, the mode of administration and the time course of treatment are at the discretion of the treating physician. Prophylactic treatments are indicated for persons at higher than average risk of getting prostate cancer, for example, persons with elevated PSA, PAP (prostate acid phosphatase) or PSP (prostate specific protein) levels. Therapeutic treatments are indicated for persons diagnosed with prostate cancer.

XII. Hormone Therapy

We have shown that prostate tumors grown in males become malignant, while those grown in females remain benign. While not wishing to be limited by theory, it is believed that this difference is due to the hormonal environment. It is believed that up-regulation of Repro-PC-1.0 expression is directly or indirectly controlled by a hormone response element that is responsive to androgens, such as testosterone, but not to estrogens. However, regardless of the exact role Repro-PC-1.0 expression plays in prostate cancer, the experiments reported herein show that altering the hormonal environment changes the character of prostate cells.

Therefore, one method for treating prostate cancer involves inhibiting contact between the prostate cancer cell and a hormone that activates hormone response elements regulating the malignant condition. In one embodiment, prostate cancer is treated by decrease the amount of testosterone in the system of the subject, or increasing the amount of estrogen. Methods for altering the hormone profile of subjects is well known in the art. For example, estrogens can be administered to increase their amount in the blood, and compounds, such as flutamide, luteinizing hormone releasing hormone (LHRH) antagonists and cyproterone acetate are known to decrease the amount of androgens in the system.

XIII. Polypeptide and Polynucleotide Vaccines Against Repro-PC-1.0

This invention also provides vaccines against Repro-PC-1.0-expressing cells and methods for using them.

In one aspect, this invention provides methods for eliciting a humoral immune response against Repro-PC-1.0. The method involves immunizing a subject with a vaccine comprising an immunogenic amount of Repro-PC-1.0 polypeptide or an immunogenic Repro-PC-1.0 analog. Such vaccines elicit antibodies against Repro-PC-1.0.

In another aspect, this invention provides methods for eliciting an MHC Class II-dependent immune response against cells expressing Repro-PC-1.0. MHC Class II molecules bind peptides having particular amino acid motifs well known in the art. The MHC Class II-dependent response involves the uptake of an antigen by antigen-presenting cells (APC's), its processing, and presentation on the cell surface as part of an MHC Class II/antigenic peptide complex. Alternatively, MHC Class II molecules on the cell surface can bind peptides having the proper motif.

Antigen presenting cells interact with CD4-positive T-helper cells, thereby activating the T-helper cells. Activated T-helper cells stimulate B-lymphocytes to produce antibodies against the antigen. Antibodies mark cells bearing the antigen on their surface. The marked cells are subject to antibody-dependent cell-mediated cytotoxicity, in which NK cells or macrophages, which bear Fc receptors, attack the marked cells.

Methods for eliciting an MHC Class Independent immune response involve administering to a subject a vaccine including an immunogenic amount of Repro-PC-1.0 polypeptide or an immunogenic Repro-PC-1.0 analog that includes an ammo acid motif recognized by MHC Class II molecules of the subject. Alternatively, antigen presenting cells can be cultured with such peptides to allow binding, and the cells can be administered to the subject. Preferably, the cells are syngeneic with the subject.

In another aspect, this invention provides methods for eliciting an MHC Class I-dependent cell-mediated immune response against cells expressing Repro-PC-1.0 in a subject. MHC Class I molecules also bind peptides having particular amino acid motifs well known in the art. Proteins expressed in a cell are digested into peptides, become associated with MHC Class I molecules and are presented on the cell surface. There, they are recognized by CD8-positive lymphocytes, generating a cytotoxic T-lymphocyte response against cells expressing the epitopes in association with MHC Class 1 molecules. Because prostate cancer cells express Repro-PC-1.0, the generation of cytotoxic T-lymphocytes that attack such cells is useful in the prophylactic or therapeutic treatment of prostate cancer.

HLA-A1 binding motif includes a first conserved residue of T, S or M, a second conserved residue of D or E, and a third conserved residue of Y. Other second conserved residues are A, S or T. The first and second conserved residues are adjacent and are preferably separated from the third conserved residue by 6 to 7 residues (SEQ ID NOS:11 and 12). A second motif consists of a first conserved residue of E or D and a second conserved residue of Y where the first and second conserved residues are separated by 5 to 6 residues (SEQ ID NOS:13 and 14). The HLA-A3.2 binding motif includes a first conserved residue of L, M, I, V, S, A, T and F at position 2 and a second conserved residue of K, R or Y at the C-terminal end. Other first conserved residues are C, G or D and alternatively E. Other second conserved residues are H or F. The first and second conserved residues are preferably separated by 6 to 7 residues (SEQ ID NOS:15 and 16). The HLA-A11 binding motif includes a first conserved residue of T or V at position 2 and a C-terminal conserved residue of K. The first and second conserved residues are preferably separated by 6 to 7 residues (SEQ ID NOS:17 and 18). The HLA-A24.1 binding motif includes a first conserved residue of Y, F or W at position 2 and a C terminal conserved residue of F, I, W, M or L. The first and second conserved residues are preferably separated by 6 to 7 residues (SEQ ID NOS:19 and 20).

A methodical way of identifying peptides that can activate a cytotoxic T-cell response is to prepare a set of overlapping fragments of the polypeptide of about 9 to 15 amino acids, and test them for the ability to stimulate T-cells. For example, the set could include fragments spanning amino acids 1–15, 2–16, 3–17, etc. Such fragments can be routinely prepared by a peptide synthesizer and can be tested in batches to decrease the amount of experimentation necessary. For example, the set of 25 overlapping fragments including fragment 1–15 to fragment 25–39 can be tested as compared to a set including fragment 26–40 to 51–65. If only one set shows activity, that set can be broken down into two smaller sets and tested again, until individual immunogenic peptides are identified.

Another method involves transfecting cells er vivo with such expression vectors, and administering the cells to the subject. The cells preferably are syngeneic to the subject.

Methods for eliciting an immune response against Repro-PC-1.0 in a subject are useful in prophylactic methods for preventing prostate cancer when the vaccine is administered to a subject who does not already suffer from prostate cancer.

This invention also provides a method for activating cytotoxic T-lymphocytes against cells that express a Repro-PC-1.0 comprising contacting T-lymphocytes ex vivo with an immunogenic peptide comprising a linear epitope derived from the Repro-PC-1.0, the peptide capable of inducing a Class I MHC-restricted cytotoxic T-lymphocyte response against cells expressing the Repro-PC-1.0.

This invention also provides a method for determining whether a cell expresses Repro-PC-1.0 polypeptide involving the steps of contacting the cell with a cytotoxic T-lymphocyte activated against cells expressing a Repro-PC-1.0 and determining whether the cytotoxic T-lymphocyte attacks the cell.

This invention also provides an immunogenic peptide comprising a linear epitope derived from the Repro-PC-1.0, the peptide capable of inducing a Class I MHC-restricted cytotoxic T-lymphocyte response against cells expressing Repro-PC-1.0. In certain embodiments, the immunogenic peptide has between 8 and 12 amino acids and the linear epitope has a Class I MHC molecule binding motif. In another embodiment, the immunogenic peptide further comprises a T helper cell epitope.

The following chart provides portions of the amino acid sequence of Repro-PC-1.0 (SEQ ID NO:2). Amino acid numbers are indicated. Bracketed bars over the amino acid sequence indicate vertebrate MHC Class I or MHC Class II binding motifs. Amino acid numbers are indicated. Peptides of about 8–15 amino acids in length that include these motifs, including peptides whose entire amino acid sequence is selected from the sequence of Repro-PC-1.0, bind to MHC molecules and can be used to induce a cell-mediated or humoral immune response against Repro-PC-1.0.

```
            |--|   |---|
  9  eefdeiptvvgifsafglvftvslfawiccq  (SEQ ID NO:21)
            19 22 25   29
```

```
                |--|
            |--|    |---|
 42 ssksnktppykfvhvlkgvdiypenlnskkkfga (SEQ ID NO:22)
            52 55    61  65
            55 58
```

```
                    |---|
114  spsdlenatpklflegekesvspes   (SEQ ID NO:23)
                    124 128
```

```
               |--|
         |--|       |--|     |---|            |--|
199 lpekkhkvktrvlrktldpafdetftfygipytqiqelalhftilsfdrfsrddiigevl  (SEQ ID NO:24)
         209       221      235 239           252
               213
```

```
              |---| |--|           |---|
259 iplsgielsegkmlmnreiikrnvrkssgrgellislcyqsttntl  (SEQ ID NO:25)
              270 274 279          290 294
```

```
              |--|       |---|
376 vldsergsrneviggqlvlgaaaegtggehwkei  (SEQ ID NO:26)
              386        394 398
```

This invention also provides a pharmaceutical composition capable of eliciting an immune response against Repro-PC-1.0 (e.g., a vaccine) comprising a pharmaceutically acceptable carrier and an immunogenic amount of a compound selected from Repro-PC-1.0, a fragment of Repro-PC-1.0, an immunogenic peptide comprising a linear epitope derived from Repro-PC-1.0, the peptide capable of inducing a Class I MHC-restricted cytotoxic T-lymphocyte response or a Class 0.11 MHC-restricted immune response against cells expressing Repro-PC-1.0.

XIV. Transgenic Non-Human Animals

This invention also provides non-human mammals transgenic for Repro-PC-1.0. As used herein, "animal transgenic for Repro-PC-1.0" refers to an animal, in particular a mammal, whose germ cells (i.e., oocytes or sperm), at least, comprise a recombinant nucleic acid molecule comprising expression control sequences operatively linked to a nucleic acid sequence encoding Repro-PC-1.0. Such animals are useful, for example, as models in the study of prostate cancer.

In one embodiment, the expression control sequences are not naturally found operatively linked to Repro-PC-1.0. In one embodiment, the recombinant nucleic acid comprises a non-native Repro-PC-1.0 coding sequence, i.e., a Repro-PC-1.0 sequence that the species does not produce in nature. In one embodiment, the Repro-PC-1.0 is a human Repro-PC-1.0. In another embodiment, the expression control sequences are non-native expression control sequences introduced into the germ cells so as to recombine with the naturally occurring gene and control its expression. Particularly useful transgenic mammals of this invention include rabbits and rodents such as mice.

The transgenic animals of this invention are produced, for example, by introducing the recombinant nucleic acid molecule into a fertilized egg or embryonic stem (ES) cell, typically by microinjection, electroporation, lipofection, particle-mediated gene transfer. The transgenic animals express the heterologous nucleotide sequence in tissues depending upon whether the promoter is inducible by a signal to the cell, or is constitutive. Transgenic animals can be bred with non-transgenic animals to produce transgenic animals with mixed characteristics.

XV. Methods for Screening for Compounds that Regulate Expression or Activity of Repro-PC-1.0

Compounds that regulate the expression or activity of Repro-PC-1.0 are candidates as therapeutic agents in the treatment of prostate cancer. This invention provides methods for determining whether a compound regulates (e.g., activates or inhibits) expression or activity of Repro-PC-1.0.

Methods for determining whether a compound regulates Repro-PC-1.0 expression involve administering to a cell or a test animal having an expressible Repro-PC-1.0 gene with the compound, and determining whether expression Repro-PC-1.0 is altered. In one embodiment, the methods involve administering the compound to a culture comprising the cell or to a test animal that has cells expressing Repro-PC-1.0, measuring the amount of the Repro-PC-1.0 polynucleotide or polypeptide in a sample from the culture or the animal, and determining whether the measured amount is different than the amount in a sample from the culture or from the animal under control conditions (e.g., to which no compound has been administered). Statistically significant ($p<0.05$) differences between the amount measured from the test sample and from the control sample are recorded and indicate that the compound alters the amount of Repro-PC-1.0 produced by the cell.

Methods for determining whether a compound regulates the biological activity of Repro-PC-1.0 involve contacting a cell that expresses Repro-PC-1.0 with the compound and determining whether Repro-PC-1.0 activity is altered. Repro-PC-1.0 has a significant level of amino acid sequence identity with the synaptotagmins: therefore it is believed that Repro-PC-1.0 functions in the membrane fusion and membrane budding reactions in exocytosis. Exocytosis is the process by which an intracellular vesicle fuses with the plasmalemma. As a result, the vesicle contents are released into the extracellular medium (secretion) and the components of the vesicle membrane become part of the plasmalemma. Some vesicles fuse with the plasmalemma constitutively, whereas others accumulate under the plasmalemma and fuse only after an appropriate stimulus. Constitutive exocytosis is used by cells for non-regulated protein secretion and for insertion of newly synthesized protein components into the plasmalemma. Regulated exocytosis is characteristic of secretory granules derived from the Golgi complex, which store concentrated secretory products, and of specialized vesicles such as synaptic vesicles, which store neurotransmitters.

Activity assays include detecting changes in the levels of secretions into the media or changes in membrane capacitance after the introduction of potential inhibitors of Repro-PC-1.0 such as anti-sense nucleotides, anti-Repro-PC-1.0 antibodies, peptide fragments of Repro-PC-1.0 or other molecules in combinatorial libraries. Immunological methods are used for detecting changes in the levels of released molecules such as, but not limited to PSA, PAP, PSP into the media, with, e.g., commercially available test kits (*J. Steroid Biochem. Molec. Biol.*, 37:849 (1990)). Neurotransmitter or ATP release can be detected by HPLC or by luciferin-luciferase assays, respectively (*Science*, 256:1820 (1992)). Alternatively, cells can be radiolabelled and the release of secretory granule contents could be measured by scintigraphy (*Cell*, 70:765 (1992)). Increased exocytosis can also be detected by monitoring increases in membrane capacitance. In this case, transmembrane current is measured using conventional whole-cell patch-clamp methods (*Neuron.* 10:21 (1993); *Nature,* 364:540 (1993)).

The compound to be tested can be selected from a number of sources. For example, combinatorial libraries of molecules are available for screening experiments. Using such libraries, thousands of molecules can be screened for regulatory activity. In one preferred embodiment, high throughput screening methods involve providing a library containing a large number of potential therapeutic compounds (candidate compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see e.g., U.S. Pat. No. 5,010,175, Furka (1991) *Int. J. Pept. Prot. Res.* 37: 487–493. Houghton et al. (1991) *Nature,* 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90:

6909–6913), vinylogous polypeptides (Hagihara et al. (1992) J. Amer. Chem. Soc. 114: 6568), nonpeptidal peptidomimetics with a Beta-D-Glucose scaffolding (Hirschmann et al., (1992) J. Amer. Chem. Soc. 114: 9217–9218), analogous organic syntheses of small compound libraries (Chen et al. (1994) J. Amer. Chem. Soc. 116: 2661), oligocarbamates (Cho, et al., (1993) Science 261:1303), and/or peptidyl phosphonates (Campbell et al., (1994) J. Org. Chem. 59: 658). See, generally, Gordon et al., (1994) J. Med. Chem. 37:1385, nucleic acid libraries, peptide nucleic acid libraries (see, e.g., U.S. Pat. No. 5,539,083) antibody libraries (see, e.g., Vaughn et al. (1996) Nature Biotechnology, 14(3): 309–314), and PCT/US96/10287), carbohydrate libraries (see, e.g., Liang et al. (1996) Science, 274: 1520–1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506, 337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin. Woburn, Mass., 433A Applied Biosystems, Foster City, Calif., 9050 Plus, Millipore, Bedford, Mass.).

In one embodiment this invention provides inhibitory compounds that inhibit expression of Repro-PC-1.0 identified or identifiable by the screening methods of this invention.

XVI. Genomics

The identification of cognate or polymorphic forms of the Repro-PC-1.0 gene and the tracking of those polymorphisms in individuals and families is important in genetic screening. Accordingly, this invention provides methods useful in detecting polymorphic forms of the Repro-PC-1.0 gene. The methods involve comparing the identity of a nucleotide or amino acid at a selected position from the sequence of a test Repro-PC-1.0 gene with the nucleotide or amino acid at the corresponding position from the sequence of native Repro-PC-1.0 (SEQ ID NO:1). The comparison can be carried out by any methods known in the art, including direct sequence comparison by nucleotide sequencing, sequence comparison or determination by hybridization or identification of RFLPs.

In one embodiment, the method involves nucleotide or amino acid sequencing of the entire test polynucleotide or polypeptide, or a subsequence from it, and comparing that sequence with the sequence of native Repro-PC-1.0. In another embodiment, the method involves identifying restriction fragments produced upon restriction enzyme digestion of the test polynucleotide and comparing those fragments with fragments produced by restriction enzyme digestion of native Repro-PC-1.0 gene. Restriction fragments from the native gene can be identified by analysis of the sequence to identify restriction sites. Another embodiment involves the use of oligonucleotide arrays. (See, e.g., Fodor et al., U.S. Pat. No. 5,445,934.) The method involves providing an oligonucleotide array comprising a set of oligonucleotide probes that define sequences selected from the native Repro-PC-1.0 sequence, generating hybridization data by performing a hybridization reaction between the target polynucleotide molecules and the probes in the set and detecting hybridization between the target molecules and each of the probes in the set and processing the hybridization data to determine nucleotide positions at which the identity of the target molecule differs from that of native Repro-PC-1.0. The comparison can be done manually, but is more conveniently done by a programmable, digital computer.

The following examples are offered by way of illustration, not by way of limitation.

EXAMPLES

Figure 1B:

I. LNCaP Tumor Xenografts Display Morphological and Metastatic Characteristics That are Dependent Upon the Environment in Which They are Generated Using a model system of LNCaP human prostate rumor cells, we raised tumors in both male and female athymic mice. The tumors, which typically took at least 2–3 months to develop into palpable masses, showed remarkably different features depending on whether they were propagated in a male or a female environment. Tumors that developed in male mice (male-LNCaP) showed extensive vascularization and morphological destruction compared to the highly regular and homogeneous composition of the tumors raised in females (female-LNCaP) (FIG. 1). Additionally, the tumors raised in male hosts had gained metastatic potential, whereas no metastases were ever detected in female mice. The differential morphologies of these tumors suggested the possibility that specific sequences involved in metastatic progression and/or angiogenesis had been induced in the male environment.

The aberrant expression of a number of oncogenes and growth factors (up-regulation) as well as tumor suppressor genes (down-regulation) has been implicated in a number of human tumors and in cancer progression in general. We therefore examined the expression of a representative panel of these sequences in order to investigate whether the differential appearance of male derived LNCaP tumors was the result of an androgen driven up- or down-regulation of a previously characterized factor. RNA isolated from male-LNCaPs, female-LNCaPs, LNCaP cells, PC-3 cells (a non-androgen responsive human prostate cell line), normal human spleen tissue and normal human liver tissue was subjected to Northern hybridization using a variety of probes for previously characterized oncogenes, growth factors and tumor suppressors. As can be seen in Table 1, there was no difference in the pattern of expression detected in male-LNCaP tumors compared to female-LNCaP tumors or to LNCaP cells grown in vitro indicating that the differentiated state of male-LNCaP tumors was not due to a differential expression of any of these more common factors.

TABLE 1

ONCOGENE EXPRESSION TO LNCaP TUMORS

| Probe | LNCaP[a] (Male) | LNCaP[b] (Female) | LNCaP[c] | PC-3[d] | Spleen[e] | Liver[f] |
|---|---|---|---|---|---|---|
| FGF, acidic | + | + | + | + | − | − |
| FGF, basic | + | + | + | + | − | − |
| PDGF, A-chain | + | + | + | + | − | + |
| PDGF, B-chain | + | + | + | + | + | + |
| PDGF-receptor | + | + | + | + | − | − |
| TGF-alpha | + | + | + | + | − | − |
| TGF-B | + | + | + | + | − | − |
| c-myc | + | + | + | + | − | − |
| EGF-receptor | + | + | + | + | − | − |
| Ha-ras | + | + | + | + | + | + |
| Ki-ras | + | + | + | + | − | − |
| NM23 | + | + | + | + | − | − |
| c-myc (oligo) | + | + | + | − | − | − |
| p53 (oligo) | + | + | + | + | + | + |
| androgen receptor (oligo) | + | + | + | + | − | − |

TABLE 1-continued

ONCOGENE EXPRESSION TO LNCaP TUMORS

| Probe | LNCaP[a] (Male) | LNCaP[b] (Female) | LNCaP[c] | PC-3[d] | Spleen[e] | Liver[f] |
|---|---|---|---|---|---|---|
| TNF-alpha (oligo) | + | + | + | + | − | + |
| TNF-B (oligo) | + | + | + | + | − | − |
| int-2 (oligo) | + | + | + | + | + | + |
| actin | + | + | + | + | + | + |
| alpha-tubulin | + | + | + | + | + | + |

Summary of Northern hybridization results for a variety of oncogene probes to 4 μg total RNA from different tissues. cell lines and tissues.
[a–f]The presence of detectable RNA was scored on a relative basis. +, detectable levels: −, undetectable levels.
[a]RNA isolated from LNCaP prostate adenocarcinoma tumors propagated in male athymic mice.
[b]RNA isolated from LNCaP prostate adenocarcinoma tumors propagated in female athymic mice.
[c]RNA isolated from LNCaP prostate adenocarcinoma cells.
[d]RNA isolated from PC-3 (non-androgen responsive) cells.
[e]RNA isolated from human spleen tissue.
[f]RNA isolated from human liver tissue.

II. Isolation of Male-LNCaP-Specific Sequences

In order to isolate sequences that are over-expressed in male-LNCaP tumors and that might elucidate the mechanism(s) responsible for the dramatic morphological differences, we generated a male-LNCaP-specific probe by three rounds of subtractive hybridization with female-LNCaP tumor cDNA. This male-LNCaP specific probe was then used to perform a primary screen of a lambda-ZAP-male-LNCaP tumor cDNA library. Positive plaques were subjected to a dual secondary screen, using the male-LNCaP specific probe and total female-LNCaP tumor cDNA. Clones were considered positive if they hybridized strongly to the "male-specific" probe and weakly to the female probe.

Figure 2A:
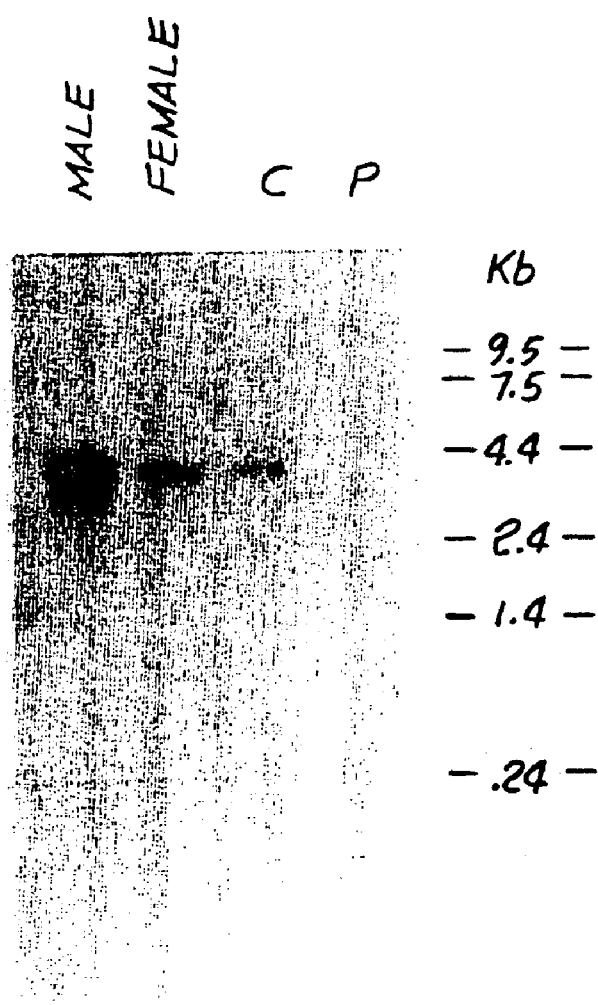
FIGS. 2A–2B are photographs of a Northern analysis.
Figure 2B:
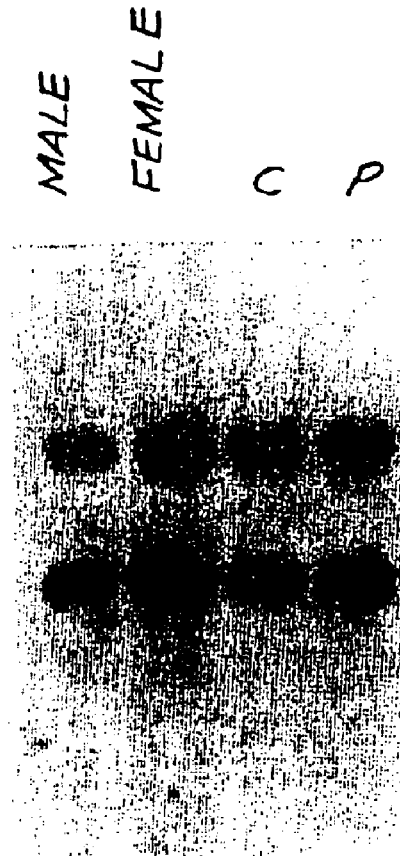

The resulting positives were subjected to a tertiary screen in which the clones were "rescued" and their plasmid DNA was subjected to duplicate Southern hybridizations using total male-LNCaP or total female-LNCaP cDNA. The DNA from clones hybridizing more strongly to male-LNCaP sequences was then subjected to Northern analyses. The DNA from one clone, Repro-PC-1.0, when hybridized to equivalent amounts of RNA from male-LNCaP tumors, female-LNCaP tumors or LNCaP cells showed an ~10× amplification of a single 4.4 kb mRNA in male-LNCaP tumors (FIG. 2a). Rehybridization of the same blot with probes for actin and tubulin showed that the amplified signal detected by Repro-PC-1.0 in male-LNCaP tumors was not due to an increased level of RNA in that lane (FIG. 2b).

III. Sequence Analysis of Repro-PC-1.0

Initial sequence analysis of clone Repro-PC-1.0 did not reveal any significant open reading frames (ORFs) in either direction. Subsequently, an overlapping clone (PS5-1), was isolated from the male-LNCaP tumor library by hybridization with an oligonucleotide probe encoding 5' sequences contained within the Repro-PC-1.0 insert. Directionality of the Repro-PC-1.0 clone was inferred from the presence of a putative poly-A tail. The complete coding region was determined by sequencing PS5-1 and an overlapping RACE-PCR derived 5' end cDNA clone. The alignment of these clones is shown in FIG. 3. Northern analyses of the 2 overlapping clones to panels of RNA isolated from male-LNCaP tumors, female-LNCaP rumors, LNCaP cells and PC-3 cells revealed the same pattern of hybridization as originally observed with Repro-PC-1.0.

Sequence analysis of the overlapping clones revealed a single 1275 bp ORF encoding 425 amino acids, followed by a 2466 bp 3' untranslated region to which a polyadenylate tail was added (SEQ ID NO: 1). The sequence obtained for the 5' untranslated region of Repro-PC-1.0 was much shorter than the approximately 750 bp of sequence predicted, based on the size of the 4.4 kb message that was observed by RNA blot hybridizations, and is therefore probably incomplete. The M, and pI were calculated to be 48,070 and 8.83, respectively.

Sequence identity and similarity were determined using the FASTDB program, Bionet suite, Oxford Molecular Group, Campbell, Calif. or BLASTX, NCBI.

Figure 4:
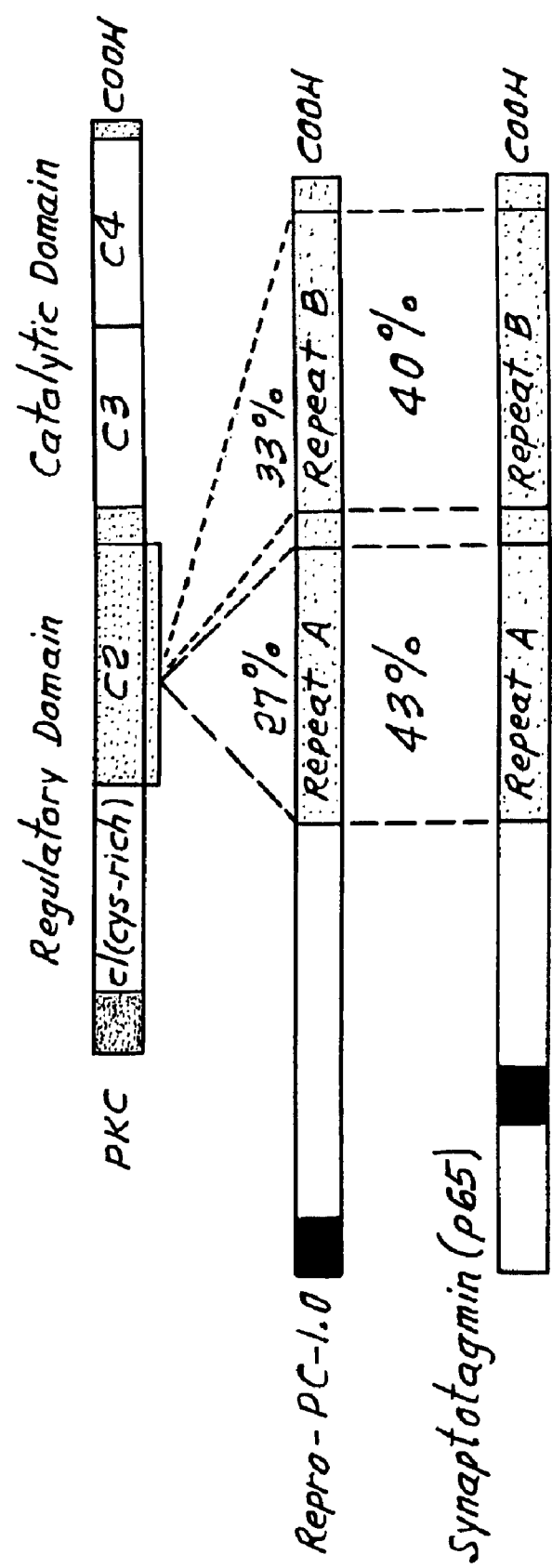
FIG. 4 presents a comparison of the organization of PKC, Repro-PC-1.0 and synaptotagmin polypeptides.

The predicted amino acid sequence of the C-terminal region of Repro-PC-1.0 contained two copies of a 116 amino acid direct repeat that had 34% identity (41% similarity) with each other. These repeats are located from amino acid 150 to 252 and amino acid 276 to 396. The repeats were found to be homologous to the C2 regulatory domain of calcium-dependent isoforms of protein kinase C (PKC), and to isoforms of synaptotagmin (FIG. 4).

Synaptotagmin is actually a family of highly conserved, abundant synaptic vesicle proteins that has been proposed to play a role in synaptic vesicle translocation to the presynaptic release sire of the plasma membrane (docking) and/or fusion of these two membranes. Structurally, synaptotagmin isoforms can be divided into several domains which include: an intravesicular, amino-terminal domain; a single transmembrane domain; and a cytoplasmic, carboxyl-terminal domain that consists of two repeats homologous to the C2 regulatory domain of PKC termed A and B (FIG. 4). Homologues of synaptotagmin have shown greater conservation of sequence identity and similarity in the cytoplasmic domain containing the two PKC C2-homologous repeats than in the N-terminal intravesicular or transmembrane domains.

FIG. 5 shows the alignment of the amino acid sequences for Repro-PC-1.0 and rat synaptotagmin IV. Repro-PC-1.0 shows 90% overall identity with rat synaptotagmin IV. Like the other synaptotagmin isoforms, Repro-PC-1.0 was most similar to these sequences in the PKC C2 repeat C-terminal region (91% identity). The two internal repeats of Repro-PC-1.0 are approximately as homologous to each other (34% identity) as to the corresponding region of PKC (identity between 35% and 43# depending on the isoform). As in the other forms of synaptotagin, the amino acid residues that are identical between the two internal repeats of Repro-PC-1.0 are also conserved between Repro-PC-1.0 and PKC, revealing a core consensus sequence of SDPY(V/I)K (SEQ ID NO:27) followed by a stretch of basic residues (FIG. 6).

Hydrophobicity plots of the amino acid sequence of Repro-PC-1.0 revealed a single segment, from residues 15–37, of sufficient length and hydrophobicity to constitute a transmembrane domain. Although this domain does nor align colinearly with the corresponding domain in the other synaptotagmins, it also displays the unusual transmembrane boundaries reported for other synaptotagmins. The N-terminal border of the putative transmembrane domain is flanked by a proline, the C-terminus of the domain is flanked by cysteine residues followed by a highly positively charged region.

IV. Chromosomal Location

Southern blot analyses of Repro-PC-1.0 hybridization to human genomic DNA revealed a non-complex pattern indicating a single copy sequence. Analysis of Repro-PC-1.0 hybridization to genomic DNAs from a panel of phylogenetically distinct species showed that the sequences encoding Repro-PC-1.0 were highly conserved, hybridizing to yeast DNA even under high stringency conditions. A single, evolutionarily conserved Repro-PC-1.0 gene localizes to chromosome 18.

V. Expression of Repro-PC-1.0 in Prostate Carcinoma and in Other Tissues

In order to compare the expression of Repro-PC-1.0 in normal prostate to prostate adenocarcinomas and benign hyperplasias, Repro-PC-1.0 sequences were specifically amplified from RNA isolated from a number of well characterized tissue sources by RT-PCR. These products were fractionated, transferred and hybridized with a Repro-PC-1.0 probe and the level of expression was graded by relative signal intensity of the Repro-PC-1.0 specific bands (Table 2).

TABLE 2

EXPRESSION OF REPRO-PC-1.0 IN PROSTATE CARCINOMA

| Tissue Source | Repro-PC-1.0 PCR Hybridization |
|---|---|
| LNCaP Tumor (male)* | +++ |
| +DNase | +++ |
| +RNase | − |
| Normal Prostate** | − |
| +DNase | − |
| +RNase | − |
| Prostate Adenocarcinoma*** | ++ |
| +DNase | + |
| +RNase | − |
| Prostatic Benign Hyperplasia | − |
| Uterus | − |

*LNCaP Tumor tissue grown in male athymic mice.
**The prostate was obtained from a 65 yr. old male, who may have had the beginning of undiagnosed prostate cancer.
***Compilation of analysis from 2 different prostate adenocarcinomas.
The level of expression was graded by relative signal intensity of the Repro-PC-1.0 specific bands:
+++ very strong hybridization
++ strong hybridization
+ moderate hybridization
− no hybridization Repro-PC-1.0 sequences were only present in the RNAs isolated from prostatic adenocarcinoma samples and were not detectable in samples representing benign hyperplasias. The marginal signal detected in normal prostate tissue may reflect the beginning of undiagnosed prostate cancer, as the source of the tissue was an elderly man. To ensure that the amplified sequences were not due to genomic DNA contaminants, control reactions were performed, adding RNase or DNase prior to the 1st strand synthesis step. As shown in Table 2, the addition of DNase had no effect of the level of signal detected in prostate adenocarcinoma samples, whereas RNase treatment eradicated the signal, indicating that the Repro-PC-1.0 hybridizing signal detected in the adenocarcinomas samples was due to Repro-PC-1.0 RNA sequences and not due to contaminating genomic sequences.

TABLE 3

REPRO-PC-1.0 mRNA IN HUMAN CELL LINES AND MAMMALIAN TISSUES

| CELL LINE EXPRESSION | TISSUE SOURCE | Repro-PC-1.0 |
|---|---|---|
| LNCaP | prostate adenocarcinoma | + |
| LNCaP | male tumors* | + |
| LNCaP | female tumors** | + |
| PC-3 | prostate carcinoma | − |
| DU-145 | prostate carcinoma | − |
| BT-20 | breast carcinoma | − |
| T-47D | breast ductal carcinoma | − |
| BT-474 | breast ductal carcinoma | − |
| MCF-7 | breast adenocarcinoma | − |
| SK-BR-3 | breast adenocarcinoma | − |
| MDA-MB-231 | breast adenocarcinoma | − |
| LS174T | colon adenocarcinoma | − |
| NIH:OVCAR-3 | ovary adenocarcinoma | − |
| 3a5 | hybridoma-SP2/0 fusion myeloma | − |
|  | placenta, human | − |
|  | pancreas, human | − |
|  | pituitary, human | − |
|  | liver, human | − |
|  | spleen, human | − |
|  | brain, human | + |
|  | heart, human | − |
|  | skeletal muscle, human | − |
|  | kidney, human | − |
|  | pancreas, canine | − |
|  | pituitary, canine | − |
|  | spleen, mouse | − |
|  | rubella (strain M33) | − |

*LNCaP xenograft tumors propagated in male athymic mice.
**LNCaP xenograft tumors propagated in female athymic mice.
Summary of Northern hybridization results for different human cell lines and mammalian tissues.
+ indicates detectable expression
− absence of detectable expression Repro-PC-1.0 expression in additional carcinomas and tissues was investigated by RNA blot analysis. Table 3 lists the different carcinoma cell lines and human tissues that were screened for Repro-PC-1.0 expression. Repro-PC-1.0 expression was not detected in any other prostate or non-prostate carcinoma cell line besides the LNCaP line, nor was it detected in any other normal tissue except for brain. Interestingly, this is precisely the tissue where the synaptotagmin family is expressed, suggesting the LNCaP cells are aberrantly expressing a gene that encodes a protein involved in the regulated secretory pathway.

VI. Differential Expression of Repro-PC-1.0 and Human Synaptotagmin

In order to address whether or not Repro-PC-1.0 might represent a human synaptotagmin isoform that was differentially expressed in LNCaP tumor cells, we compared the expression of Repro-PC-1.0 and human synaptotagmin in LNCaP cells, brain tissue, PC12 cells (rat adrenal medullary cell line) and in a non-Repro-PC-1.0 or -synaptotagmin expressing human carcinoma cell line, RL95-2. RNA isolated from each of these sources was hybridized to either Repro-PC-1.0-specific or human synaptotagmin-specific probes. Both forms are detectable in RNA isolated from normal human brain, but only Repro-PC-1.0, and not human synaptotagmin is expressed in LNCaP cells. Interestingly, only Repro-PC-1.0 sequences are detectable in PC12 cells which normally express rat brain synaptotagmin I. Rat brain synaptotagmin I would not have been detectable with either the human synaptotagmin-specific or Repro-PC-1.0-specific probes. The cross hybridization of Repro-PC-1.0 to PC12 RNA suggests that a rat homologue of Repro-PC-1.0 might also be expressed in PC12 cells and may participate in regulated secretion. Thus Repro-PC-1.0 expression is specifically and differentially up-regulated in LNCaP tumor cells, representing a novel human brain synaptotagmin isoform that cross hybridizes with a rat homologue, distinct from rat brain synaptotagmin I, normally expressed in PC12 cells.

VII. Discussion

Tumor-specific proteins permit insight into the mechanisms that contribute to the progression to malignancy. The LNCaP cell line provides a useful model of prostate cancer that has proven valuable in understanding prostate cancer. These cells were used to raise human prostate rumor xenografts in both male and female athymic mice. Our initial observations of host-sex-dependent histological and morphological differences in tumor production prompted us to investigate these two forms of tumor as a potential source of RNA to develop a subtractive screen for identifying uniquely expressed proteins in a tumor that has progressed through vascularization (angiogenesis) and has gained metastatic character.

Tumorigenesis is often associated with either an activation of an oncogene or the inactivation of a tumor-suppressor gene (anti-oncogene). We compared the level of expression of a number of oncogenes, rumor suppressor genes, growth factors and the androgen receptor between the irregular LNCaP tumors grown in a male environment, to LNCaP tumors grown in a female environment, to LNCaP cells grown in vitro, to another non-androgen responsive human prostate cancer cell line and to normal human tissue. Because tumors grown in male hosts showed a profile that was similar to tumors grown in females and to LNCaP cells grown in vitro, we considered the two morphologically distinct tumors as a suitable source of potential message.

VII. Fluorescent In Situ Hybridization (FISH) of Metaphase Chromosomes

Cultured lymphoblast cells are incubated with BrdU and Nacadozole for 3 to 5 hours prior to harvesting with trypsin and collection by centrifugation. The cells are resuspended in KCl and fixed in suspension with methanol/acetic acid on ice for 30 min. The cell suspension is placed on microscope slides and slowly dried at 70° C., 80% humidity. A biotinylated cDNA probe, complementary to Repro-PC-1.0, is generated using standard protocols (Labeling and calorimetric detection of non-isotopic probes. In "Current Protocols in Molecular Biology," F. M. Ausubel, et al., Eds., pp. 3, 18, 1–3,18.7, John Wiley and Sons, Inc., New York). The biotinylated probe is diluted to 3 ng/ul in a hybridization buffer containing 50% formamide, 10% dextran, 2×SSC, 50 μg/ml Cot-1 DNA and incubated overnight at 37° C. with the fixed cell spread which has been preincubated with hybridization buffer. The slides are washed twice with 0.5×SSC at 70° C., once with 4×SSC at room temperature, once with antibody diluent (1% BSA, 4×SSC) at room temperature for 5 min. and incubated for 20 min. at 37° C. with FITC-conjugated avidin diluted (10 μg/ml) in antibody diluent. The slides are washed three times with a buffer containing 4×SSC, then with a buffer containing 4×SSC, 0.05% Tween20, then with a buffer containing 4×SSC followed by counter staining for 2 min with DAPI (200 ng/ml in 4×SSC) and washing with 4×SSC. The excess fluid is blotted off and the slides are mounted with a FITC stabilizing reagent containing p-phenylenediamine dihydrochloride in 90% glycerol. The hybridization profile is determined using a fluorescent microscope.

IX. PCR Mimic Quantitation Protocol

The following protocol is useful for amplifying Repro-PC-1.0 from a cell sample.

A. RNA Extraction:

1. Prostate is removed from patient
2. Within 15–30 minutes of the prostate being removed from patient, identify normal and cancerous areas and remove approximately 100–300 mg of tissue (approximately 1 cm×0.5 cm×0.4 cm) from each area.
3. If RNA is to be extracted at a later time, then place each tissue chunk in a prelabeled piece of heavy duty aluminum foil and immediately drop into liquid nitrogen.
4. Store the tissues in the −70° C. freezer.
5. The embedded portions are sectioned and given to the pathologist for assessment.
6. The rest of the prostate is fixed in formaldehyde.
7. When ready for use, extract the RNA as follows:
8. Drop the frozen tissue into 3 ml Trizol (GIBCOBRL, catalog number 15596-018) and homogenize using a Polytron, Tissumizer or another adequate tissue homogenizer.
9. Incubate homogenized sample for 5 minutes at room temperature.
10. Add 600 μl chloroform (200 μl chloroform per ml Trizol).
11. Mix for IS seconds and allow to sit at room temperature for 2–3 minutes.
12. Spin at 12000×g for 15 minutes at 4° C.
13. Carefully remove the upper, colorless aqueous phase.
14. Precipitate the RNA using an equal volume of isopropanol.
15. Allow samples to sit at room temperature for 10 minutes.
16. Spin at 12000×g for 15 minutes at 4° C.
17. Remove the supernatant and wash the pellet, by breaking up the pellet and pipetting up and down, with ice-cold 75% ethanol in RNase-free water.
18. Spin at 12000×g for 15 minutes at 4° C.
19. Remove the supernatant and dry pellet in Speed-Vac for 2–3 minutes.
20. Resuspend the RNA in RNase-free water and incubate at 65° C. for 10 minutes.
21. Take OD readings at 260 and 280 nin (for concentrated samples, a 1:125 dilution of the sample should be used to read the OD values. The conversion factor thus would be the $A_{260}$ of the sample multiplied by the dilution factor of 125 multiplied by 40 μg/ml (Sample $A_{260}$ × 125×40 μg/ml).

B. DNase Treatment:

The RNA samples should be DNAse I treated (GIBCOBRL, catalog number 18068-015) prior to use in cDNA synthesis and PCR in order to get rid of any contaminating genomic DNA. DNase treat the samples as follows:

1. To a microfuge tube add:

| Component | Sample | No RT control |
|---|---|---|
| 5 μg total RNA | x μl | x μl |
| 10X DNase I reaction buffer | 1 μl | 1 μl |
| DNase I (1 unit/μl) | 2 μl | 1 μl |
| DEPC water | to 10 μl | to 10 μl |

2. Incubate tubes for 15 minutes at room temperature.
3. Inactivate the DNase I by adding 1 μl of 25 mM EDTA.
4. Heat for 10 minutes at 65° C.

C. cDNA Synthesis:
Reverse transcribe RNA as follows:
1. In an microfuge tube mix the following:

| Component | Sample | No RT control |
|---|---|---|
| 5 μg total RNA | 10 μl | 10 μl |
| Random hexamers (50 ng/μl) | 2 μl | 2 μl |
| DEPC water | 0 μl | 0 μl |

2. Incubate at 70° C. for 10 minutes and ice-quench for 2 minutes.
3. In a microfuge tube prepare the following reaction mixture in the order indicated:

| Component | Per reaction add |
|---|---|
| 10X PCR buffer | 2 μl |
| 25 mM MgCl$_2$ | 2 μl |
| 10 mM dNTP mix (10 mM each dATP, dCTP, dGTP and dTTP) | 1 μl |
| 100 mM DTT | 2 μl |

Note*
Make enough of the above mix for one extra reaction

4. Add 7 μl of the above mixture to each of the RNA/random hexamers mixture.
5. Mix and centrifuge briefly.
6. Incubate at room temperature for 5 minutes
7. ADD 1 μl (200 units) of SUPERSCRIPT II RT (GIBCOBRL, catalog number 18064-014), mix and incubate at room temperature for 10 minutes (do not add RT to No RT control tube).
8. Transfer tubes to 42° C. and incubate for 50 minutes.
9. Terminate reactions by incubating at 70° C. for 15 minutes.
10. Chill on ice for 2 minutes and centrifuge briefly.
11. Add 1 μl of RNase H (GIBCOBRL, catalog number 18021-022) and incubate or 20 minutes at 37° C.

D. Mimic Construction:
Make the mimic dilution series as follows:
1. Label eight 0.5 ml microcentrifuge tubes 1–8.
2. Prepare a 100 attomole/μl stock for each of the mimics. All dilutions should be made in mimic dilution solution (i.e. TE containing 10 μg/ml of nucleic acid grade glycogen):
   Prepare 20 μl of a 1:10 dilution of the 100 attomole/μl stock and label this tube as 10 attomole/μl.
   Add 18 μl of mimic dilution solution to tube 1 and add 2 μl from the 10 attomole/μl tube. To make the twofold serial Prepare 20 μl of a 1:10 dilution of the 10 attomole/μl stock and label this tube as "1".
3. Prepare the rest of the mimic stock solutions as follows:

| Concentration (attomole/μl): | Tube label | |
|---|---|---|
| 1 | 1 | Add 2 μl of 10 attomole/μl tube to 18 μl of mimic dilution solution, and change pipet tip |
| 0.5 | 2 | Add 10 μl from tube 1 to 10 μl of mimic dilution solution, mix and change pipet tip |
| 0.25 | 3 | Add 10 μl from tube 2 to 10 μl of mimic dilution solution, mix and change pipet tip |
| 0.125 | 4 | Add 10 μl from tube 3 to 10 μl of mimic dilution solution, mix and change pipet tip |
| 0.05 | 5 | Add 8 μl from tube 4 to 12 μl of mimic dilution solution, mix and change pipet tip |
| 0.025 | 6 | Add 10 μl from tube 5 to 10 μl of mimic dilution solution, mix and change pipet tip |
| 0.0125 | 7 | Add 10 μl from tube 6 to 10 μl of mimic dilution solution, mix and change pipet tip |
| 0.005 | 8 | Add 8 μl from tube 4 to 12 μl of mimic dilution solution, mix and change pipet tip |

Summarized in the table below are the molar and mass concentrations for the solution series of G3PDH (glyceraldehyde 3-phosphate dehydrogenase and PC1:

| Tube Number | MIMIC | PC1 1524–2156 | G3PDH 71–1030 |
|---|---|---|---|
| | MIMIC Size | 486 bp | 630 bp |
| | Master Stock Conc. | ng/μl | ng/μl |
| | 100 attomoles = | 32 pg | 42 pg |
| | cDNA Size | 657 bp | 983 bp |
| | MIMIC: Dilution Series attomoles/μl | | |
| | 100 | 32 pg/μl | 42 pg/μl |
| | 10 | 3.2 pg/μl | 4.2 pg/μl |
| 1 | 1 | 320 fg/μl | 420 fg/μl |
| 2 | 0.5 | 160 fg/μl | 210 fg/μl |
| 3 | 0.25 | 80 fg/μl | 105 fg/μl |
| 4 | 0.125 | 40 fg/μl | 52.5 fg/μl |
| 5 | 0.05 | 16 fg/μl | 21 fg/μl |
| 6 | 0.025 | 8 fg/μl | 10.5 fg/μl |
| 7 | 0.0125 | 4 fg/μl | 5.25 fg/μl |
| 8 | 0.005 | 1.6 fg/μl | 2.1 fg/μl |

III PCR:

Set up the PCR as follows:

| Component | Final concentration | Volume per 25 μl reaction |
|---|---|---|
| 10X PCR buffer | 1X | 2.5 μl |
| 25 mM MgCl$_2$ | 1.5 mM | 1.5 μl |
| 2.5 mM dNTP mix (mix made by adding equal volumes of 10 mM dATP, dTTP, dCTP and dGTP) | 200 mM | 2.0 μl |
| Upper primer (100 ng/μl) | 200 nM | 0.4 μl |
| Lower primer (100 ng/μl) | 200 nM | 0.4 μl |
| Mimic | varies | 1 μl |
| cDNA | N/A | 1 μl |

-continued

| Component | Final concentration | Volume per 25 μl reaction |
|---|---|---|
| Taq polymerase (5 U/μl) | 0.05 U/μl | 0.25 μl |
| ddH₂O | N/A | 15.95 μl |

1. Number the wells of a PCR plate or PCR tubes 1–8.
2. Add 1 μl of the mimic corresponding to the number on tube (e.g. tube #1 gets 1 μl of mimic #1 and so on). Keep plate or tube on ice.
3. Make up the following mix (make enough mix for a+1 reactions, i.e. 9 reactions). Keep mix tube on ice:

| Component | Volume per 25 μl reaction | Volume per 9 × 25 μl reaction |
|---|---|---|
| 10X PCR buffer | 2.5 μl | 22.5 μl |
| 25 mM MgCl₂ | 1.5 μl | 13.5 μl |
| 2.5 mM dNTP mix (mix made by adding equal volumes of 10 mM dATP, dTTP, dCTP and dGTP) | 2.0 μl | 18 μl |
| Upper primer (100 ng/μl) | 0.4 μl | 3.6 μl |
| Lower primer (100 ng/μl) | 0.4 μl | 3.6 μl |
| cDNA | 1 μl | 9 μl |
| Taq polymerase (5 U/μl) | 0.25 μl | 2.25 μl |
| ddH₂O | 15.95 μl | 143.6 μl |

4. Add 24 μl to each of the wells or rube to which the mimic had already been added in step 2 above. Keep plate or rube on ice while adding the mix.

5. Perform PCR using the following cycle:

| Cycle | Process | Time (minutes) | Temperature (° C.) |
|---|---|---|---|
| Hold 1 | Denaturation | 5 | 94 |
| 2 | Denaturation | 0.5 (30 seconds) | 94 |
| 3 | Annealing | 1 | 55 |
| 4 | Extension | 2 | 72 |
| 5–34 | Repeat cycles 2–4 34 times | | |
| Hold 2 | Long Extension | 5 | 72 |
| Hold 3 | Cold | until plate is removed | 4 |

6. Run 10 μl of the product on a 2% TAE agarose gel with 1 kb ladder as marker.

The present invention provides novel polynucleotides encoding a prostate tumor-specific maker, Repro-PC-1.0, the protein encoded by it, and methods for using these materials. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A method for detecting a polypeptide of SEQ ID NO:2 in a sample, comprising the steps of:

(a) contacting the sample with an antibody that specifically binds to the said polypeptide and (b) detecting specific binding between the antibody and the said polypeptide, whereby specific binding provides a detection of the said polypeptide in the sample.

2. A method for use in the diagnosis of prostate cancer in a subject comprising the steps of:

(a) detecting a diagnostic amount of mRNA of SEQ ID NO:1 or polypeptide of SEQ ID NO:2 in a sample from the subject; and (b) comparing the diagnostic amount with a normal range of SEQ ID NO:1 mRNA or SEQ ID NO:2 polypeptide in a non-cancerous control sample, whereby a diagnostic amount above the normal range provides a positive indication in the diagnosis of prostate cancer.

3. The method of claim 2 wherein the sample is blood, urine, lymph node tissue or prostate tissue.

* * * * *